(12) United States Patent
Stewart

(10) Patent No.: US 7,794,657 B2
(45) Date of Patent: Sep. 14, 2010

(54) PHASE CHANGE SENSOR

(75) Inventor: Ray F. Stewart, Redwood City, CA (US)

(73) Assignee: Cantimer, Inc., Menlo Park, CA (US)

( * ) Notice: Subject to any disclaimer, the term of this patent is extended or adjusted under 35 U.S.C. 154(b) by 14 days.

(21) Appl. No.: 10/857,634

(22) Filed: May 28, 2004

(65) Prior Publication Data

US 2005/0164299 A1 Jul. 28, 2005

Related U.S. Application Data

(60) Provisional application No. 60/475,637, filed on Jun. 3, 2003.

(51) Int. Cl.
*G01N 7/00* (2006.01)
*G01N 27/00* (2006.01)
*G01N 27/22* (2006.01)
*G01N 33/48* (2006.01)

(52) U.S. Cl. .............. 422/82.01; 422/50; 422/68.1; 436/148; 436/149

(58) Field of Classification Search ............... 422/68.1; 436/148
See application file for complete search history.

(56) References Cited

U.S. PATENT DOCUMENTS

| | | | |
|---|---|---|---|
| 3,260,104 A | 7/1966 | King, Jr. | |
| 3,765,414 A * | 10/1973 | Arlen | 424/424 |
| 3,947,401 A * | 3/1976 | Stamberger | 523/106 |
| 4,361,026 A | 11/1982 | Muller et al. | |
| 4,708,019 A | 11/1987 | Rubner et al. | |
| 4,830,855 A | 5/1989 | Stewart | |
| 4,912,032 A | 3/1990 | Hoffman et al. | |
| 4,935,634 A | 6/1990 | Hansma et al. | |
| 5,120,349 A | 6/1992 | Stewart et al. | |

(Continued)

FOREIGN PATENT DOCUMENTS

EP 0 205 815 B1 7/1991

(Continued)

OTHER PUBLICATIONS

Miyata, T., et al., *Nature* 399:766-769, (1999).

(Continued)

*Primary Examiner*—Unsu Jung
(74) *Attorney, Agent, or Firm*—Judy M. Mohr; King & Spalding LLP

(57) ABSTRACT

A device is disclosed which is a highly sensitive and selective sensor. The device is comprised of a sensor material secured into a fixed position on substrate, a deformable arm and a signaling component which creates a detectable signal in response to movement of the arm. The sensitivity of the device is enhanced by using a sensor material which undergoes a dramatic change in volume which may be accompanied by a phase change in response contact with a target such a molecule of interest. The selectivity of the device is enhanced by incorporating highly specific binding receptors (e.g. antibodies) into the sensor material which receptors bind to specific targets (e.g. peptide epitopes). The binding of the target molecule to the receptor causes the sensor material to change dramatically in volume thereby moving the arm causing the signaling component (e.g. a piezoresistor) to create a detectable signal (e.g. change in resistance) thereby indicating the present of the target.

16 Claims, 11 Drawing Sheets

U.S. PATENT DOCUMENTS

| | | |
|---|---|---|
| 5,229,606 A | 7/1993 | Elings et al. |
| 5,266,801 A | 11/1993 | Elings et al. |
| 5,294,537 A | 3/1994 | Batt |
| 5,320,947 A | 6/1994 | Cheever et al. |
| 5,321,977 A | 6/1994 | Clabes et al. |
| 5,345,815 A | 9/1994 | Albrecht et al. |
| 5,345,816 A | 9/1994 | Clabes et al. |
| 5,359,021 A * | 10/1994 | Weinschenk et al. ......... 526/264 |
| 5,376,790 A | 12/1994 | Linker et al. |
| 5,400,647 A | 3/1995 | Elings |
| 5,445,008 A | 8/1995 | Wachter et al. |
| 5,461,274 A | 10/1995 | Yuji et al. |
| 5,483,822 A | 1/1996 | Albrecht et al. |
| 5,536,963 A | 7/1996 | Polla |
| 5,665,882 A | 9/1997 | Chung et al. |
| 5,679,888 A | 10/1997 | Tohda et al. |
| 5,719,324 A | 2/1998 | Thundat et al. |
| 5,744,794 A | 4/1998 | Michie et al. |
| 5,760,675 A | 6/1998 | Lee et al. |
| 5,783,332 A | 7/1998 | Amine et al. |
| 5,840,338 A | 11/1998 | Roos et al. |
| 5,854,078 A | 12/1998 | Asher et al. |
| 5,877,411 A | 3/1999 | Namerikawa et al. |
| 5,955,659 A | 9/1999 | Gupta et al. |
| 6,016,686 A | 1/2000 | Thundat |
| 6,041,642 A | 3/2000 | Duncan |
| 6,051,380 A | 4/2000 | Sosnowski et al. |
| 6,109,852 A | 8/2000 | Shahinpoor et al. |
| 6,177,282 B1 * | 1/2001 | McIntyre ................... 436/518 |
| 6,180,309 B1 | 1/2001 | Maty et al. |
| 6,183,097 B1 | 2/2001 | Saif et al. |
| 6,190,605 B1 | 2/2001 | Cadle et al. |
| 6,196,052 B1 | 3/2001 | May et al. |
| 6,200,198 B1 | 3/2001 | Ukai et al. |
| 6,201,980 B1 | 3/2001 | Darrow et al. |
| 6,280,776 B1 | 8/2001 | Sha et al. |
| 6,280,971 B1 | 8/2001 | Wang et al. |
| 6,287,765 B1 | 9/2001 | Cubicciotti |
| 6,289,717 B1 | 9/2001 | Thundat et al. |
| 6,440,788 B2 | 8/2002 | Mandelman et al. |
| 6,447,887 B1 | 9/2002 | Claus et al. |
| 6,470,575 B2 | 10/2002 | Huang et al. |
| 6,475,750 B1 | 11/2002 | Han et al. |
| 6,510,468 B1 | 1/2003 | Hayne |
| 6,514,689 B2 | 2/2003 | Han et al. |
| 6,520,339 B1 | 2/2003 | Conway, Jr. |
| 6,523,392 B2 | 2/2003 | Porter et al. |
| 6,528,026 B2 | 3/2003 | Hajduk et al. |
| 6,553,318 B2 | 4/2003 | Mansky |
| 6,823,717 B2 | 11/2004 | Porter et al. |
| 6,854,317 B2 | 2/2005 | Porter et al. |
| 6,866,819 B1 | 3/2005 | Chandra et al. |
| 7,168,294 B2 | 1/2007 | Porter et al. |
| 2002/0031841 A1 * | 3/2002 | Asher et al. ................. 436/518 |
| 2003/0010097 A1 | 1/2003 | Porter et al. |
| 2003/0137216 A1 | 7/2003 | Tamayo de Miguel et al. |
| 2006/0042416 A1 | 3/2006 | Yoon et al. |
| 2006/0053871 A1 | 3/2006 | Porter et al. |
| 2007/0119236 A1 | 5/2007 | Porter et al. |

FOREIGN PATENT DOCUMENTS

| | | |
|---|---|---|
| GB | 1 506 473 | 4/1978 |
| GB | 2 047 093 A | 11/1980 |
| GB | 2 090 264 A | 7/1982 |
| GB | 2 235 462 A | 3/1991 |
| JP | 2000-214072 A | 8/2000 |
| WO | WO89/07117 A1 | 8/1989 |

OTHER PUBLICATIONS

Hilt, Z., et al., *Mat. Res. Soc. Symp. Proc.*, 729:U4.8.1-U4.8.6, (2002).

Johannsmann, D. et al., "Visco-elastic Properties of Thin Films Probed with a Quartz Crystal Resonator", *Makromol. Chem., Macromol. Symp.*, 46:247-251 (1991).

Kanazawa et al., "The Oscillation Frequency of a Quartz Resonator in Contact with a Liquid", *Analytica Chimica Acta*, 175:99-105 (1985).

Kuckling, D. et al. "Temperature Sensitive Polymers Based on 2-(dimethyl maleinimido)-N-ethyl-acrylamide: Copolymers with N-isopropylacrylamide", *Polymer Bulletin*, 44:269-276 (2000).

Matsuda, K. et al., "A New Composite Resistor with PTC Anomaly", *Journal of Polymer Science,* Polymer Chemistry Addition, 19:1871-1873 (1981).

Michels, A. et al., "1 MHz quartz length extension resonator as a probe for scanning near-field acoustic microscopy", *Thin Solid Films*, 264:172-175 (1995).

Plate, N. A. and Shibaev, V.P., "Comb-Like Polymers. Structute and Properties", *Journal of Polymer Science Macromolecular Reviews*, 8:117-253 (1974).

* cited by examiner

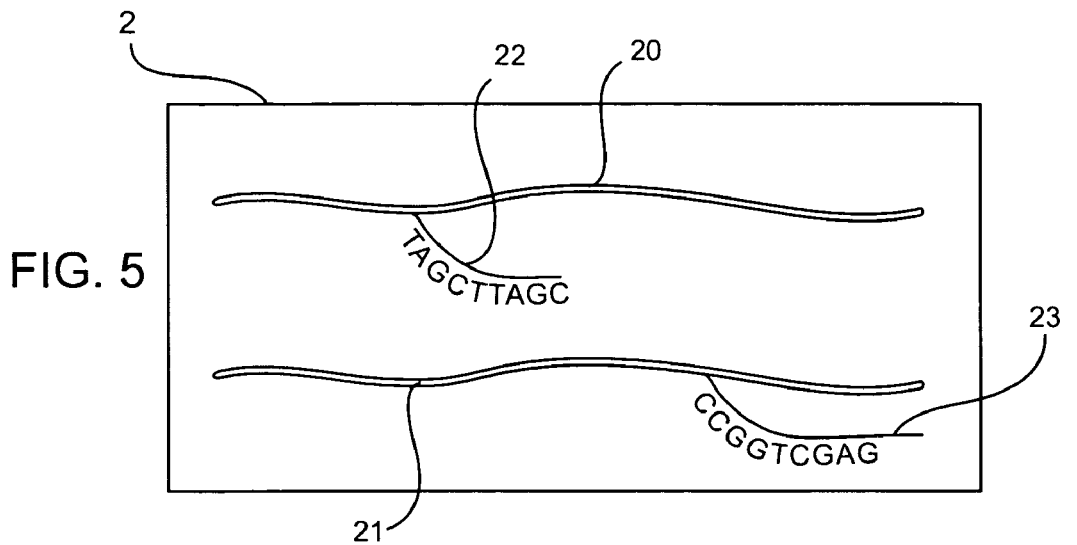
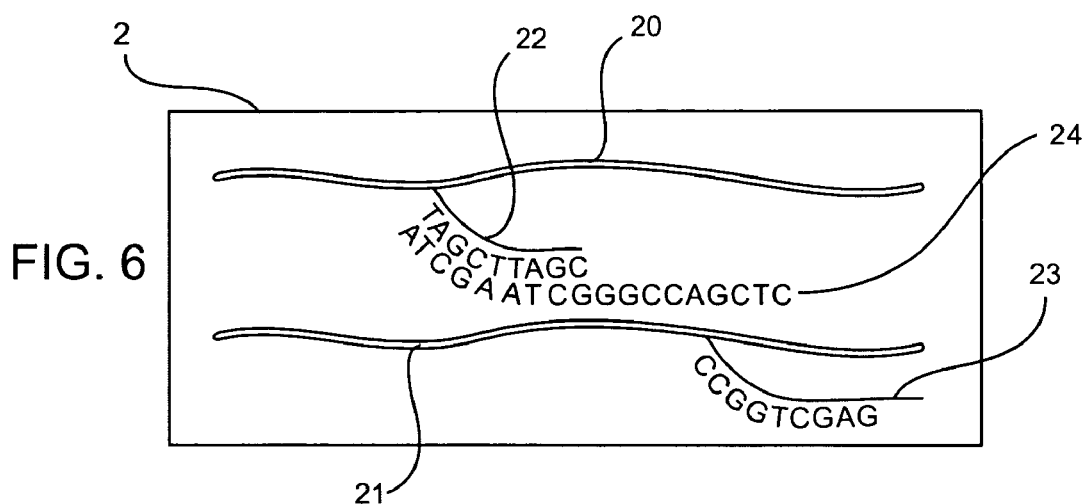
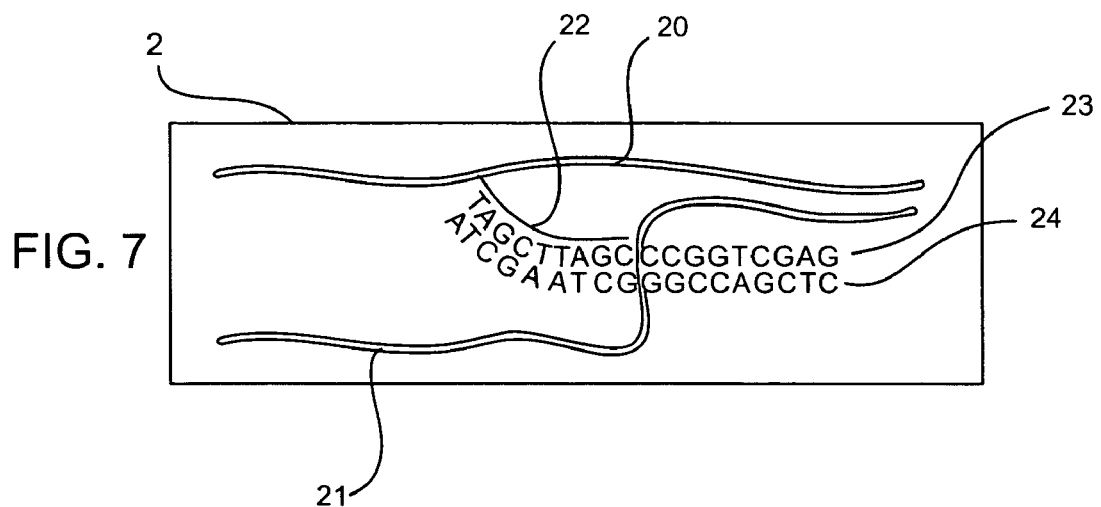

Swelling of crosslinked polyacrylamide (Soil Moist) in a series of hypotonic NaCl solutions Swelling Ratio of BM09-012 Polymer Films as a Function of Osmolality in NaCl Solutions.

Swelling Ratio of BM09-019 "Conditioned" Polymer Films as a Function of Osmolality in NaCl Solutions.

Swelling Ratio of BM09-019 "Conditioned" Films as Function of Cycling Through Osmolality

Swelling Ratio of BM09-032 HPA Homopolymer Films as a Function of Osmolality in NaCl Solutions Swelling Ratio of BM09-032 HPA Homopolymer Films as Function of Cycling Through Osmolality Equilibrium Water Absorption of BM09-032 HPA Homopolymer at 100 mOsm, as a Function of pH

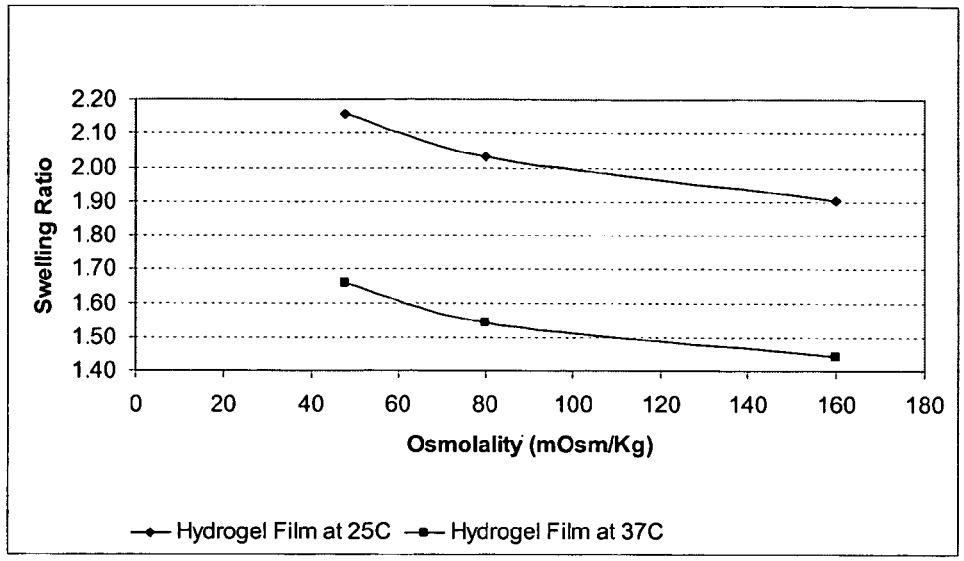
Figure 15. Plot of swelling ratio of hydroxypropyl acrylate/acrylamide hydrogel versus osmolality.
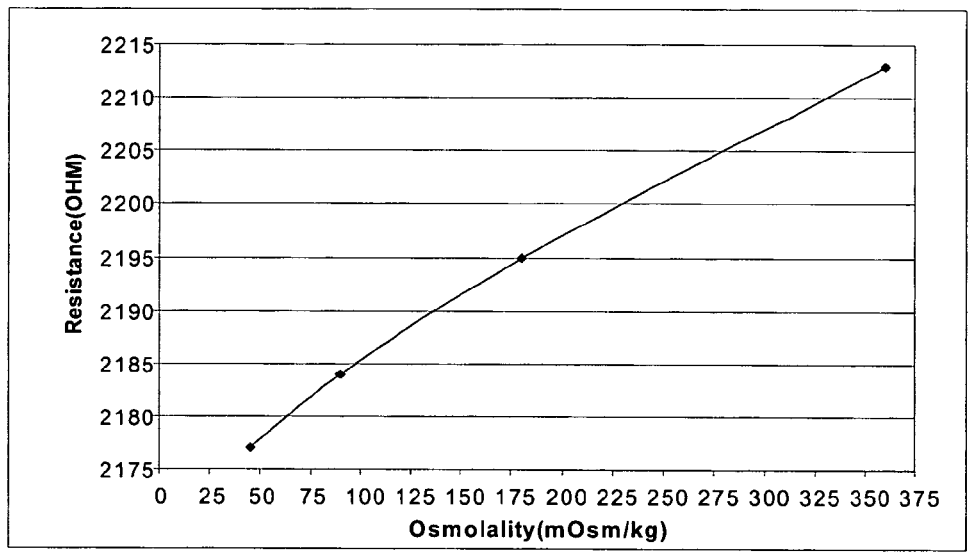
Figure 16. Plot of steady state resistance values measured at each successive osmolality concentration.

Figure 17. Overlay Plot of DSC Scans of Swollen Hydrogels Showing LCST Transition.
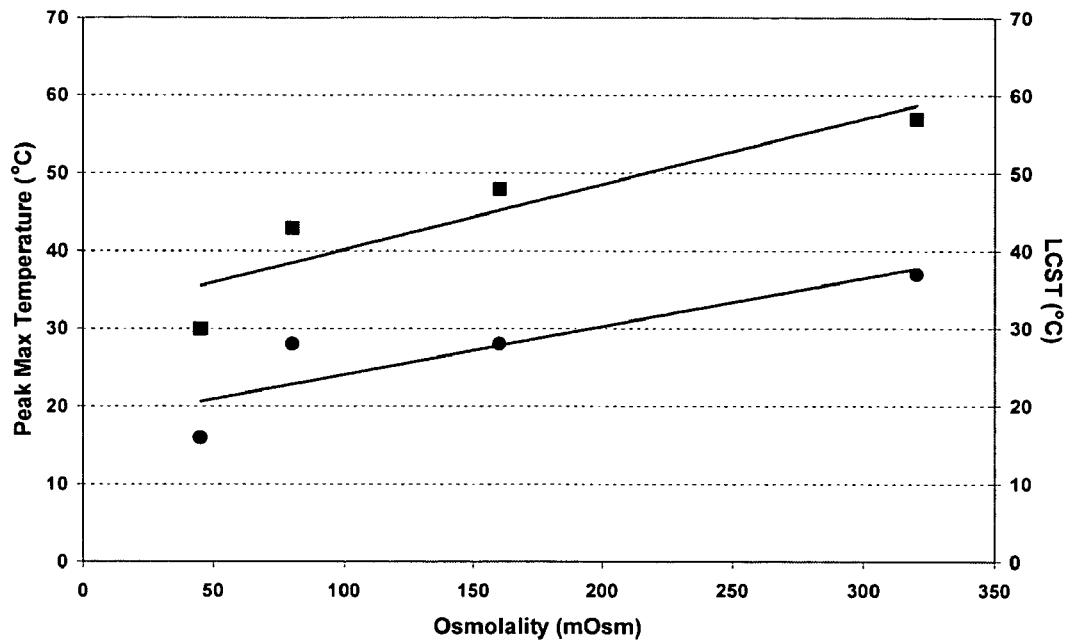
Figure 18. Least Squares Linear Plots of Peak Maximum and Lower Critical Solution Temperatures (LCST) as a Function of Osmolality.
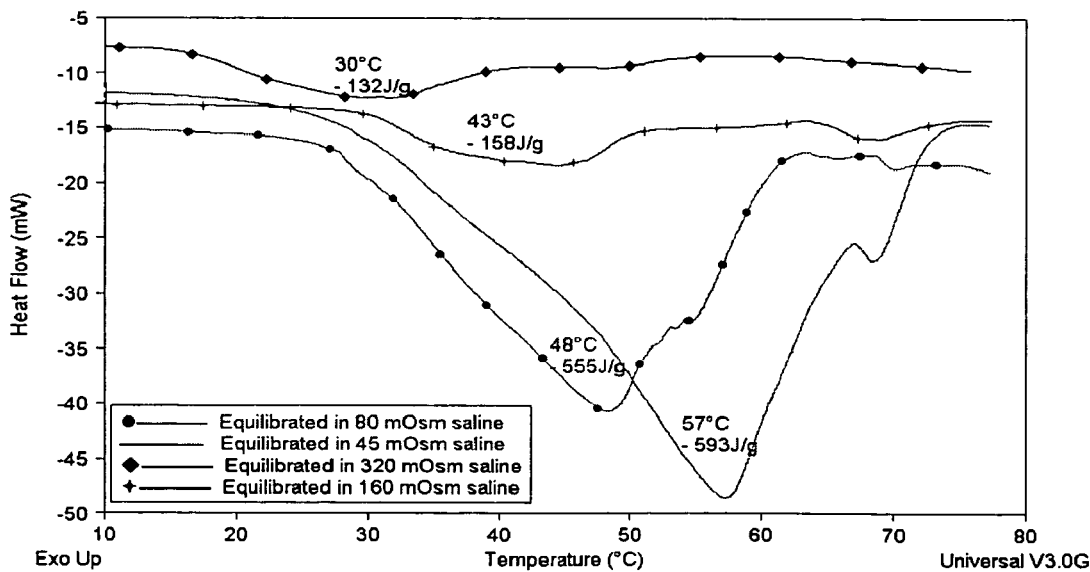

PHASE CHANGE SENSOR

CROSS-REFERENCE

This application claims the benefit of U.S. Provisional Application No. 60/475,637, filed Jun. 3, 2003 which application is incorporated herein by reference.

STATEMENT REGARDING GOVERNMENT INTEREST

This work was supported in part by the U.S. Army SBIR Grant number DAMD17-03-C-0013. Accordingly the United States government has certain rights in this invention.

FIELD OF THE INVENTION

This invention relates generally to the field of high sensitivity sensors and detection devices and more specifically to such devices which include a MEMS detector, such as a cantilever arm.

BACKGROUND OF THE INVENTION

Non-aligned probes have been developed for atomic force microscopy (AFM), including strain gauge cantilever probes containing piezoelectric or piezoresistive material which produces a change in voltage or resistance in response to cantilever bending. Such probes were first disclosed in U.S. Pat. Nos. 5,229,606 and 5,266,801 and have since also described in U.S. Pat. Nos. 5,345,816, 5,345,815 and 5,321,977. Non-aligned STM probes and piezoresistive cantilever probes are used in the AutoProbe™ VP UHV AFM/STM sold by Park Scientific Instruments.

Atomic Force Microscopes are devices that provide three dimensional topographic images of surfaces. These devices are capable of providing resolution to atomic dimensions of surface features. In an Atomic Force Microscope (AFM), an extremely sharp tip is mounted on a small flexible lever. The tip is positioned on a surface such that the attractive forces between the surface and the tip and the repulsive force of the surface on the tip are very close to equilibrium so that the force of the tip on the surface is extremely low. If the tip is scanned laterally across a sample, the deformation of the tip will vary with the surface structure and this modulation versus lateral scan position can be used to produce an image of the surface. More typically, the sample may be servoed up and down such that the tip deformation (and thus the tip force) is kept constant during lateral scanning and the vertical adjustment signal versus lateral scan position produces a topographic map of the surface. A microscope of this type is described in U.S. Pat. No. 4,935,634, by Hansma et al. The deformation of the tip can be sensed in various ways, such as using the tunneling effect off the backside of the tip as described in a patent by Binnig, optical means such as beam deformation as described in Hansma, or interferometry. Typically, most AFMs mount the tip on a low spring-constant cantilever and sense deformation by monitoring the change in angle of reflected light off the backside of the cantilever. AFMs can operate directly on insulators as well as conductors and, therefore, can be used on materials not directly accessible to other ultra-high resolution devices such as Scanning Electron Microscopes (SEMs) or Scanning Tunneling Microscopes (STMs).

The tip in an AFM must be positioned with extreme accuracy in three dimensions relative to a sample. Motion perpendicular to the sample (z-axis) provides surface profile data. Motion parallel to the surface generates the scanning. In a typical system, the image is developed from a raster type scan, with a series of data points collected by scanning the tip along a line (x-axis), and displacing the tip perpendicularly in the image plane (y-axis); and, repeating the step and scan process until the image is complete. The precise positioning in x, y, and z is usually accomplished with a piezoelectric device. Piezoelectric devices can be made to expand or contract by applying voltages to electrodes that are placed on the piezoelectric material. The motions produced by these piezoelectric scanners can be extremely small, with some scanners having sensitivities as low as tens of angstroms per volt. The total deformation possible for these scanners is typically less than 200 microns. Scanners with different sensitivities are used for different applications, with low sensitivities used for atomic resolution images, and higher sensitivity scanners used for lower resolution, larger area images. The design of the piezoelectric scanners, including the shape of the scanner and the placement of electrodes, is well known in the art.

In an AFM, either the sample can be attached to the scanner and the tip held stationary or the tip can be attached to the scanner and the sample fixed. Typically, most existing AFMs scan the sample. This invention will describe, and the drawings will represent the case where the sample is scanned; but, the invention applies equally well to either case.

As the sample is scanned in x and y, the z axis movement is closely coupled to the tip deformation. In an AFM, either the tip deformation can be monitored as the sample is scanned, or the Z position can be varied to maintain the deformation constant with feedback. This constant deformation is called the setpoint and can be set by the control system. Modulating the z position with feedback is useful for controlling and minimizing the contact force between tip and sample, and also allows the AFM to be used for other measurements, such as stiffness.

Scanning Probe Microscopes (SPMs) scan sharp probes over a sample surface and make local measurements of the properties of a sample surface. One common example is the atomic force microscope, also known as the scanning force microscope, that scans a sharp stylus attached to a flexible spring lever (commonly called a cantilever) over a sample surface. By measuring motion, position or angle of the free end of the cantilever, many properties of a surface may be determined including surface topography, local adhesion, friction, elasticity, the presence of magnetic or electric fields, etc. Other SPMs include the scanning tunneling microscope, the scanning near-field optical microscope, the scanning capacitance microscope, and several others.

One example of a delicate probe is the cantilever chip used in atomic force microscopy. The typical cantilever is 10-500 micrometers long, 10-50 micrometers wide and 0.5-5 micrometers thick, and the cantilever is often fabricated on a support substrate that is roughly 1.5 mm long, 3 mm wide, 0.5 mm high. Cantilevers are also formed out of single wires or thin metal beams, etc. Because of the delicate nature of the probes and the alignment described below, replacement of the probe in some SPM designs may take many minutes, as described in U.S. Pat. No. 5,376,790, assigned to Park Scientific Instruments. During this time, the SPM instrument is usually unavailable for use, so minimal probe exchange and alignment time is essential for high sample throughput. As scanning probe microscopes become more and more widely used, there is increasing pressure to develop instruments that can be operated more quickly and used by less-skilled operators, or even driven automatically without operator intervention.

In an attempt to solve this problem U.S. Pat. No. 5,760,675 issued Jun. 2, 1996 provides an ultra-thin Mo—C film with a thickness as small as 0.15 nanometers that still maintains an electrical continuity. The film can be prepared on insulating or semiconducting substrates of flat surface by the sputtering method using a Mo—C target directly, or by a reactive-sputtering method with a Mo target in an ambient $Ar/C_2H_2$ mixture gas at a wide range of substrate temperature.

The electrically continuous and ultra-thin Mo—C film is sensitive to a mechanical force per unit area because it is ultra-thin and there are few atoms sustaining the force. When the Mo—C film has a thickness of only a few atomic distance, for example, about 1 nanometer, the extremely small mechanical stress/strain can change the atomic distances in the film enough to affect the electrical conductivity of the film, because the distance between atoms is the crucial factor of the electrical conductivity for a given material. Therefore, this ultrathin Mo—C film can serve as an excellent piezoresistive material.

Another aspect of the Mo—C film which is crucial to such a piezo-device is that the ultra-thin Mo—C can be easily prepared on substrates with any flat surfaces of insulator or semiconductor. The film's quality of piezoresistivity is very weakly dependent on the stoichiometry of $Mo_{0.5}+xC_{0.5-x}$ within the moderate range up to x=0.25 and the deposition temperature as well as the substrate. These properties are essential to the fabrication of such integrated circuits.

U.S. Pat. No. 5,266,801 makes use of the piezoelectric or piezoresistive materials to measure the strain on the cantilever, but it still has the noise problem left irresolvable for the signal along the connecting wire. Also, the exterior transfer and processing circuit occupies a relatively large space and complicates the system structure.

U.S. Pat. No. 5,400,647 measures, by using an Atomic Force Microscope, the transverse force which is related to the magnitude of the frictional force. The Atomic Force Microscope makes use of an optical way of measuring the deformation of the cantilever. Similar to other prior art Atomic Force Microscopes, since they have many optical elements, their system spaces are relatively large, their structures are relatively complicated, and the noise problems of their connecting wires still exist.

U.S. Pat. No. 5,468,959 is a method for measuring the surface not the particular elements of the probe apparatus itself. Although the patent does mention the probe, however, this probe is not the focus of the patent. This patent mainly describes the use of capacitor and electro-static force, and the measurement of displacements and external electro-static force.

Another suitable MEMS detector for use in this invention comprises a resonating element wherein the resonate frequency of the resonator is a sensitive function of it's mass. Two primary types of resonators have been utilized previously, microcantilevers and miniature tuning forks. U.S. Pat. No. 5,719,324 (Thundat 1998) discloses micorcantilevers modified with selective binding agents and methods for measuring the resonate frequency or deflection. U.S. Pat. No. 6,289,717 (Thundat 2001) describes a sensor apparatus using a microcantilevered spring element having a coating of a detector molecule such as an antibody or antigen. A sample containing a target molecule or substrate is provided to the coating. The spring element bends in response to the stress induced by the binding which occurs between the detector and target molecules. Deflections of the cantilever are detected by a variety of detection techniques. The microcantilever may be approximately 1 to 200 micrometers long, approximately 1 to 50 micrometers wide, and approximately 0.3 to 3.0 micrometers thick. A sensitivity for detection of deflections is in the range of 0.01 nanometers.

U.S. Pat. No. 6,528,026 whish describes devices and methods for measuring the properties of combinatorial arrays of polymers using resonators which may include miniature tuning forks. This system is particularly useful for measuring intrinsic polymer properties such as Tg and molecular weight. Other publications cited in the '026 patent include "The Oscillation Frequency of a Quartz Resonator in Contact with a Liquid," K Keiji Kanazawa and Joseph G. Gordon II, Analytica Chimica Acta, vol. 175, pp. 99-105, 1985. 1 MHz quartz length extension resonator as a probe for scanning near-field acousitic microscopy, Thin Solid Films, A. Michels, F. Meinen, T. Murdfield, W. Gohde, U. C. Fischer, E. Beckmann and H. Fuchs, vol. 264, pp. 172-195, 1995. Piezoelectric quartz resonators or mechanical oscillators can be used to evaluate the viscosity of reaction mixtures, as well as a host of other material properties, including molecular weight, specific gravity, elasticity, dielectric constant, and conductivity. In a typical application, the mechanical oscillator, which can be as small as a few mm in length, is immersed in the reaction mixture. The response of the oscillator to an excitation signal is obtained for a range of input signal frequencies, and depends on the composition and properties of the reaction mixture. By calibrating the resonator with a set of well characterized liquid standards, the properties of the reaction mixture can be determined from the response of the mechanical oscillator. Further details on the use of piezoelectric quartz oscillators to measure material properties are described in co-pending U.S. patent application Ser. No. 09/133,171 "Method and Apparatus for Characterizing Materials by Using a Mechanical Resonator," filed Aug. 12, 1998, which is herein incorporated by reference.

Although many different kinds of mechanical oscillators currently exist, some are less useful for measuring properties of liquid solutions. For example, ultrasonic transducers or oscillators cannot be used in all liquids due to diffraction effects and steady acoustic (compressive) waves generated within the reactor vessel. These effects usually occur when the size of the oscillator and the vessel are not much greater than the characteristic wavelength of the acoustic waves. Thus, for reactor vessel diameters on the order of a few centimeters, the frequency of the mechanical oscillator should be above 1 MHz. Unfortunately, complex liquids and mixtures, including polymer solutions, often behave like elastic gels at these high frequencies, which results in inaccurate resonator response.

Often, shear-mode transducers as well as various surface-wave transducers can be used to avoid some of the problems associated with typical ultrasonic transducers. Because of the manner in which they vibrate, shear mode transducers generate viscous shear waves instead of acoustic waves. Since viscous shear waves decay exponentially with distance from the sensor surface, such sensors tend to be insensitive to the geometry of the measurement volume, thus eliminating most diffraction and reflection problems. Unfortunately, the operating frequency of these sensors is also high, which, as mentioned above, restricts their use to simple fluids. Moreover, at high vibration frequencies, most of the interaction between the sensor and the fluid is confined to a thin layer of liquid near the sensor surface. Any modification of the sensor surface through adsorption of solution components will often result in dramatic changes in the resonator response.

U.S. Pat. No. 6,553,318 describes methods to measure various physical properties of polymers using resonators cites therein "Visco-elastic Properties of Thin Films Probed with a Quartz Crystal Resonator," D. Johannsmann, F. Embs, C. G.

Willson, G. Wegner, and W. Knoll, Makromol. Chem., Macromol. Symp., vol. 46, 1991, pp. 247-251

Recently researchers at Arizona State University have referred to a miniature tuning fork based sensor using polymer "wires".

Their work refers to the use of a chemical vapor sensor by using a quartz tuning fork array. The sensor array is based on the detection of mechanical response of thin polymer wire stretched across the two prongs of quartz tuning forks (2 mm×1 mm×0.2 mm). When the fork is set to oscillate, the wire is stretched and compressed by the two prongs, showing a resonance spectrum of unique features. Upon exposure to the analyte, the polymer mechanical properties are changed and a frequency and/or amplitude shift takes place in an extension proportional to the analyte concentration. Every fork of the array is modified with a particular polymer wire and oscillates with its proper frequency. So, a multiple-peak spectrum is obtained when a linear frequency sweep is applied. After chemical vapor injection, some of the polymer wires suffer chemical absorption and the resulting spectrum changes allow us to discriminate the nature of the chemical vapor. Their work shows testing of five different polymer materials to sense different polar and non-polar vapors. The responses towards ethanol vapor injections with various concentrations have been demonstrated and very low detection limits were achieved.

SUMMARY OF THE INVENTION

A device is disclosed which is a highly sensitive and selective sensor. The device is comprised of a sensor material secured into a fixed position on a substrate, a deformable arm and a signaling component which creates a detectable signal in response to movement of the arm. The sensitivity of the device is enhanced by using a sensor material which undergoes a dramatic change in volume such as a phase change in response to a target molecule of interest. The selectivity of the device is enhanced by incorporating highly specific binding receptors (e.g. antibodies) into the sensor material which receptors bind to specific targets (e.g. peptide epitopes). The binding of the target molecule to the receptor causes sensor material to undergo a phase change which moves the arm causing the signaling component (e.g. a piezoresistor) to create a detectable signal (e.g. change in resistance) thereby indicating the present of the target.

Devices of the invention specifically encompass resonators including a tuning fork (where the polymer spans the two forks) or a resonator attached to a substrate to which the polymer is attached. Putting a resonator into a hydrogel provides a very sensitive detection means as the internal viscosity of the hydrogel changes. The invention also specifically includes a resonator coated with phase change polymer wherein the device (coated resonator) is placed into an environment such as water having an analyte. Such a system performs well for either a hydrogel or a crystalline or glassy polymer maintained at a static temperature or subjected to a controlled temperature ramp.

An aspect of the invention is a device capable of detecting a wide range of target molecules with a high degree of sensitivity and selectivity.

Another aspect of the invention is that the sensor material undergoes a dramatic change in volume whereby a hydrogel sheet about 5, 10, 20, 50 or 100 microns thick expands or contracts 0.5% or more, 1% or more, 5% or more, or 10% or more and is detected by the arm capable of detecting movement of in a range of 1 to 1,000 angstroms or more which may include a phase change.

Another aspect of the invention is that the sensor material comprise a highly specific binding receptor such as a monoclonal antibody or nucleotide sequence which only binds to a single target and not to other molecules which may be closely related to the target.

Yet another aspect of the invention is a signaling component which undergoes a change such as a change in resistance, resonant frequency, electrical output, or capacitance in response to very small movements of the arm, or the case of a resonator, to the rheological properties of the materials it is contact with.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 5 is a schematic view of a sensing material showing two fibers with each attached to a receptor nucleotide sequence.

FIG. 6 is a schematic view of the materials of FIG. 5 with a target sequence bound to a receptor sequence.

FIG. 7 is a schematic view of the material of FIG. 6 with the target sequence bound to each of the two receptor sequences thereby causing a shrinkage of the material as the fibers are pulled together.

FIG. 15 is a graph of the swelling ratio versus osmolality.

FIG. 16 is a graph of resistance versus osmolality.

FIG. 17 is a graph of temperature versus osmolality.

FIG. 18 is a graph of heat flow versus temperature.

DETAILED DESCRIPTION OF THE INVENTION

Figure 1:
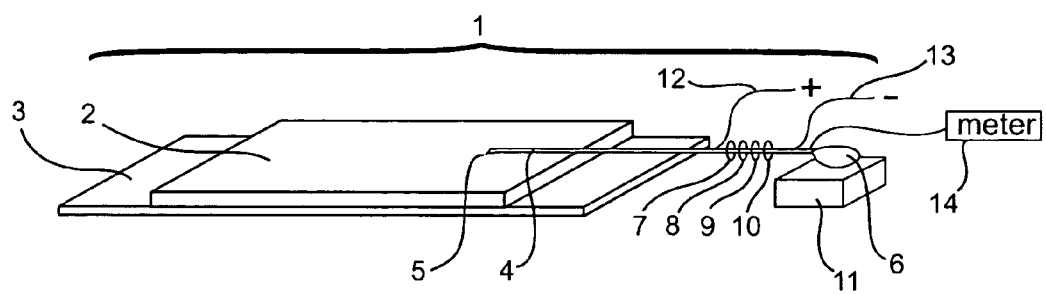
FIG. 1 is a perspective view of an embodiment of a sensor device of the invention.

Before the present sensor material, sensor device and methods are described, it is to be understood that this invention is not limited to particular materials and embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a receptor" includes a plurality of such receptors and reference to "the hydrogel" includes reference to one or more hydrogels and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "antibody" is meant an immunoglobulin protein which is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest which may be the target molecule.

Antibodies used in the invention to connect to the sensor material are immunoreactive or immunospecific for and therefore specifically and selectively bind to a target molecule. Antibodies which are immunoreactive and immunospecific for on a single target molecule are preferred. Antibodies for antigens of known pathogenic bacteria and viruses are preferably immunospecific—i.e., not substantially cross-reactive with related materials. Although the term "antibody" encompasses all types of antibodies (e.g., monoclonal) the antibodies used with the invention are preferably monoclonal and reproducible.

By "purified antibody" is meant one which is sufficiently free of other proteins, carbohydrates, and lipids with which it is naturally associated. Such an antibody "preferentially binds" to a target molecule such as a peptide or protein (or an antigenic fragment thereof), i.e., does not substantially recognize and bind to other antigenically unrelated molecules. A purified antibody used with the sensor material of the invention is preferably immunoreactive with and immunospecific for a single target molecule or portion thereof on the surface of a pathogenic microorganism of a specific species of microorganism.

By "antigenic fragment" is meant a portion of such a protein which is capable of binding an antibody used with the sensor material of the invention.

By "binds specifically" is meant high avidity and/or high affinity binding of an antibody to a specific polypeptide i.e., epitope of a particular target molecule such as a target protein. Antibody binding to its epitope on this specific polypeptide is preferably stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a target molecule with a binding affinity of $10^7$ liters/mole or more, preferably $10^8$ liters/mole or more are said to bind specifically to a target molecule of interest. In general, an antibody with a binding affinity of $10^6$ liters/mole or less is not useful in that it will not bind an antigen at a detectable level using conventional methodology currently used.

By "detectably labeled antibody", is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labelling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)).

The terms "phase change" and "phase transition" are used interchangeably here and include evaporation, melting and freezing of water, the formation of frost and snow, and the sublimination of dry ice which are well-known phenomena, and are examples of five of the six common changes in state:
 (i) melting of a solid into a liquid
 (ii) freezing of a liquid into a solid
 (iii) evaporation of a liquid into a gas
 (iv) condensation of a gas into a liquid
 (v) the vaporization (sublimination) of a solid into a gas
 (vi) the freezing of a vapor into a solid The changes are listed in parts in which each process of the pair is the reverse of the other. When the substance has polymorphic solid forms such as a hydrogel, other phase transitions are possible, such as
 vii) transition from solid I into solid II
 (viii) transition from solid II into solid I (ix) melting from solid II into liquid (x) freezing liquid into solid II, etc.

(xi) With respect to certain solids, including polymeric materials, a specific phase transition of interest is the Glass Transition (Tg). The Tg is commonly designated as that temperature at which the onset of molecular motion is observed. Tg's may be measured by for example, differential scanning calorimetery, dynamic mechanical spectroscopy, dielectric spectroscopy and other know methods.

Another phase change of interest in polymeric systems is the melting point. Because polymers are usually statistical mixtures of individual components they typically have broader melting point ranges than pure elements or compounds. Melting points of polymers, including gels, can be measured by calorimetric methods, for example differential scanning calorimetry, or by optical methods or mechanical methods.

Water undergoes a phase change not only from gas to liquid to solid (ice) but from ice I to ice II to ice III, ice IV to ice V to ice VI to ice VII. A sensor material of the invention such as a hydrogel may undergo a phase change of one gel phase to another phase when contacted with a target molecule.

As used herein the term "piezoresistive" refers to a material having an electrical resistance which decreases in response to compression caused by mechanical pressure applied thereto in the direction of the current path. Such piezoresistive materials can be, for example, resilient cellular polymer foams with conductive coatings covering the walls of the cells.

"Resistance" refers to the opposition of the material to the flow of electric current along the current path in the material and is measured in ohms. Resistance increases proportionately with the length of the current path and the specific resistance, or "resistivity" of the material, and it varies inversely to the amount of cross sectional area available to the current. The resistivity is a property of the material and may be thought of as a measure of (resistance/length)/area. More particularly, the resistance may be determined in accordance with the following formula:

$$R=(\rho L)/A \quad (I)$$

where

R=resistance in ohms $\rho$=resistivity in ohm-inches

L=length in inches

A=area in square inches

The current through a circuit varies in proportion to the applied voltage and inversely with the resistance, as provided in Ohm's Law:

$$I=V/R \quad (II)$$

where

I=current in amperes

V=voltage in volts

R=resistance in ohms

Typically, the resistance of a flat conductive sheet across the plane of the sheet, i.e., from one edge to the opposite edge, is measured in units of ohms per square. For any given thickness of conductive sheet, the resistance value across the square remains the same no matter what the size of the square is. In applications where the current path is from one surface to another of the conductive sheet, i.e., in a direction perpendicular to the plane of the sheet, resistance is measured in ohms.

Specific Embodiments

FIG. 1 shows a perspective, schematic view of an embodiment of a sensor device 1 of the invention. The device 1 is comprised of a sensor material 2 connected, secured, attached or anchored in place in some manner such as to a substrate 3. An arm 4 is positioned over the sensor material 2 and an end 5 of the arm 4 is positioned very close to a surface of the sensor material 2 such as 1 mm or less, or 0.1 mm or less or 1 micrometer or less. Thus, when the sensor material 2 expands it moves the end 5 of the arm 4. Conventional microcantilever sensor devices are disclosed in U.S. Pat. No. 6,523,392 issued Feb. 25, 2003 and U.S. Patent Publication No. 2003/0010097 published Jan. 16, 2003. These designs may be changed to include sensor material 2 of the present invention.

The arm 4 may be comprised of a suitable material such as silicon or variation or analog thereof such as silicon nitride which may be heated and drawn into a thin strand. The arm 4 may be formed from and integral with a base 6 comprised of the same material. One or more signaling components such as the four signaling components 7, 8, 9, and 10 are present on or in the arm 4. The base 6 is connected, attached, secured or anchored in some manner to the substrate 11. Accordingly, when the sensor material 2 expands it moves the arm 4 via contact with the end 5. Because the sensor material 2 is secured to the substrate 3 and the base 6 of the arm is secured to the substrate 11 the arm 4 bends. The bending of the arm 4 causes physical force such as compression to be applied to the signaling components 7, 8, 9 and 10. Resistors can be easily and inexpensively manufactured and a piezoresistor can be designed to be very sensitive to changing resistance in response to small degrees of physical force. The piezoresistor may be comprised of barium titanate.

Electrical connections 12 and 13 connect to the arm 4 at two points and make it possible to run a current between those two points. The current run through the signaling components 7-10 and is detected by the meter 14. Various types of meters can be used, e.g. volts, meters, amp meters, etc. The meter 14 can show, for example, a small change in current caused by a small change in resistance caused by a small bending of the arm 4 caused by a small expansion of the sensor material 2. The signaling components 7-10 may be a piezoresistor, piezoelectric component, a capacitor or combinations thereof. There may be one signaling component, two, three, four or more. When more than one is present they may be identical or different such that they respond to and send signals at different levels of movements of the arm 4.

Figure 2:
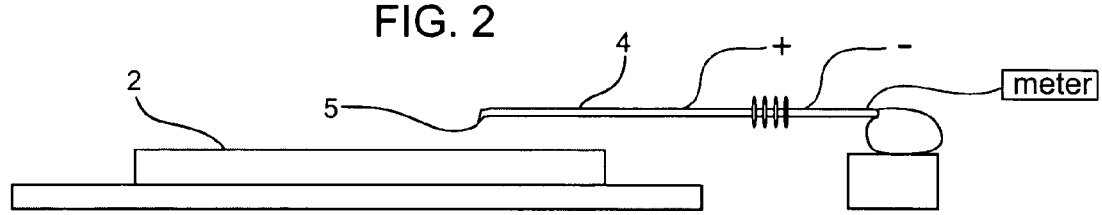
FIG. 2 is a side view of the embodiment of FIG. 1 showing the cantilever arm not in contact with the sensor material.
Figure 3:
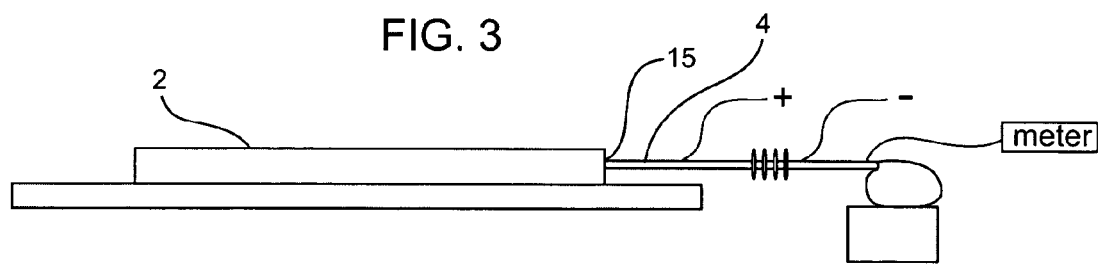
FIG. 3 is a side view of another embodiment of the sensor device of the invention with an end of the cantilever arm attached to the sensor material.

FIG. 2 is a schematic side view showing the end 5 of the arm 4 not in contact with the surface of the sensor material 2. The end 5 of the arm 4 is sufficiently close to the surface of the material 2 that a small expansion of the material 2 causes contact with the end 5 and movement of the arm 4. However, if the sensor material 2 were to decrease in size in response to a target the end 5 would not be effected. This draw back is dealt with in the embodiments of FIGS. 3 and 4.

Figure 4:
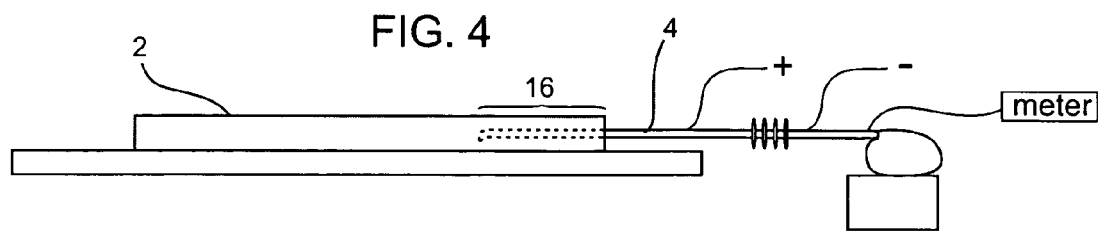
FIG. 4 is a side view of yet another embodiment of the sensor device of the invention with a portion of the cantilever arm contained within a portion of the sensor material.

The end 15 of the arm 4 is attached to a surface of the sensor material 2. Thus, when the sensor material 2 undergoes any volumetric change (expansion or reduction in size) the end 15 is effected and the arm 4 is moved. In a somewhat similar manner a portion 16 of the arm 4 may be inside the material 2 as shown in FIG. 4. Those skilled in the art reading this disclosure will recognize that other arrangements of the components are possible and are within the scope of the present invention. For example, the end 5 of FIG. 1 may be placed into contact with the sensor material 2 in a manner such that the arm 4 is in a bent position with end 5 held in a forced up position by a surface of the sensor material 2. In such a configuration shrinkage of the material 2 causes movement of the end 5 and relaxes the bend in the arm 4 which can be detected by the signaling components 7-10. Different configurations and positioning of signaling components 7-10 are also considered to be within the scope of the present invention. For example, signaling components may be equally spaced along the length of the arm 4, positioned at either end or located at points in the arm where maximum bending of the arm 4 has been determined to occur in response to movement of the sensor material 2.

In addition to changing the number and positioned of the signaling component it is possible to configure the device to include two, three, four, five or more arms which are positioned in the same manner or are independently positioned relative to each other and the sensor material 2. The number and positioning of the signaling components and arms can effect the overall sensitivity of the device. However, the sensitivity of the device is usually effected more by the nature of the sensor material 2. The sensor material is a material which undergoes a dramatic change in volume, e.g. 20% or more, 50% or more, 100% or more. The change may be an expansion or contraction. Although the sensor material may be a wide range of different materials one class of such is a hydrogel. Information relating to and examples of hydrogels are provided below.

Hydrogels

Hydrogels are three dimensional networks of hydrophilic polymers which have been tied together to form water-swellable but water insoluble structures. The term hydrogel is to be applied to hydrophilic polymers in a dry state (xerogel) as well as in a wet state. These hydrogels can be tied together in a number of ways. Firstly, radiation or radical cross-linking of hydrophilic polymers, examples being poly(acrylic acids), poly(methacrylic acids), poly(hydroxyethylmethacrylates), poly(glyceryl methacrylate), poly(vinyl alcohols), poly(ethylene oxides), poly(acrylamides), poly(N-alkylamides), poly(N,N-dimethylaminopropyl-N'-acrylamide), poly(ethylene imines), sodium/potassium poly(acrylates), polysaccharides e.g. xanthates, alginates, guar gum, agarose etc., poly(vinyl pyrrolidone) and cellulose based derivatives. Secondly, chemical cross-linking of hydrophilic polymers and monomers, with appropriate polyfunctional monomers, examples include poly(hydroxyethylmethacrylate) cross-linked with suitable agents, the copolymerisation of hydroxyethylmethacrylate monomer with dimethacrylate ester crosslinking agents, poly(ethylene oxide) based polyurethanes prepared through the reaction of hydroxyl-terminated poly(ethylene glycols) with polyisocyanates or by the reaction with diisocyanates in the presence of polyfunctional monomers such as triols, and cellulose derivates cross-linked with dialdehydes, diepoxides and polybasic acids. Thirdly, incorporation of hydrophilic monomers and polymers into block and graft copolymers, examples being block and graft copolymers of poly(ethylene oxide) with suitable polymers, poly(vinyl pyrrolidone)-co-polystyrene copolymers, polyurethanes and polyurethaneureas and polyurethaneureas based on poly(ethylene oxide), polyurethaneureas and poly(acrylonitrile)-co-poly(acrylic acid) copolymers, and a variety of derivatives of poly(acrylontriles), poly(vinyl alcohols) and poly(acrylic acids). Fourthly molecular complex formation between hydrophilic polymers and other polymers, examples being poly(ethylene oxides) hydrogel complexes with poly(acrylic acids) and poly(methacrylic acids). Lastly, entanglement cross-linking of high molecular weight hydrophilic polymers, examples being hydrogels based on high molecular weight poly(ethylene oxides) admixed with polyfunctional acrylic or vinyl monomers.

It is possible to produce hydrogels which are physically extremely weak when swollen in water so that they flow either under their own weight or under low shear. However, the preferred hydrogels are characterized in that when swollen fully with water they do not flow under their own weight. Preferably they have also significant strength so that they can transmit the osmotic pressure which develops within their structure when they swell in water. A further desirable but not essential feature is that they are tough and not brittle materials in the dry (or xerogel) non-hydrated state; that is xerogel materials which exhibit a glass transition temperature ($T_g$) well below ambient temperature are preferred. Preferably the $T_g$ is below conceivable use temperatures of the sensor. Many hydrogel materials have high $T_g$ values well above ambient temperatures and may be brittle and weak in use on extreme flexing. They can, however, be utilized as such extreme flexing is rarely encountered.

A preferred group of hydrophilic polymer comprising hydrogels are Poly(ethylene glycols) (PEGs) based hydrogels either crosslinked or made as chain-extended or block copolymers. Such crosslinked copolymers can be made via the reaction of the hydrogel ends of the PEGs with a diisocyanate and a polyol. These are known as polyurethanes and are described for example in UK Patent No. GB 2047093B, UK Patent No. 1506473, European Patent Application Publication No. 0205815 and International Patent Application (PCT) Publication No. WO89/07117. The block copolymers of PEGs can also be made utilising only difunctional units such as, for example, a combination of poly(ethylene glycol), poly(propylene glycol), a diisocyanate and optionally a diamine.

A further preferred group of hydrophilic polymer comprising hydrogels are based on linear chain-extended poly(ethylene oxide) polyurethaneurea hydrogels (UK GB22354620) and a series of linear poly(ethylene oxide)-co-poly(propylene oxide) block copolymer polyurethaneurea hydrogels. These polyurethaneurea (PUU) materials are able to absorb and swell in aqueous media, while retaining their mechanical integrity. The degree to which the polymeric hydrogels will absorb and swell with aqueous solutions is determined by the amount of hydrophilic poly(ethylene oxide) (PEO) incorporated within their structures. The higher the PEO content, the greater the swellability of the hydrogel material. The PUU hydrogels, when swollen, can have equilibrium aqueous media contents ranging from 5-95% by weight at ambient temperature. The hydrogels also exhibit changes in swelling with variations in temperature and may be described as "temperature responsive hydrogels."

As a result of their linear structure and chemical composition, the PUU hydrogels are soluble in a number of relatively "mild" organic solvents such as methanol, ethanol, propan-2-ol, methyl ethyl ketone, dichloromethane and chloroform. The solubility of the PUU hydrogels means that they can be readily fabricated into films or devices by solvent casting techniques or used in coating applications. The absorption of aqueous media by the PUU hydrogels produces an increase in their physical dimensions and this change can be used to exert a mechanical force or pressure. The speed and extent of the swelling and dimensional response of the PUU hydrogels is determined by their degree of hydrophilicity, governed by the PEO content, their physical dimensions and to the temperature of the system. The poly(ethylene oxide) based PUU hydrogel systems have an inverse swelling response in aqueous media with increasing temperature. A swollen PUU hydrogel will decrease in swelling as the temperature of the system is increased. The decrease in swelling of the PUU hydrogel will result in a contraction of the physical dimensions of the material which can be used to produce a mechanical response. The hydrogels described can be manufactured by various known processes and have the advantage that they are solvent soluble and therefore can be made in a form suitable for coating. They are also thermoplastic and may be extruded into fibres from the melt (with or without plasticizers). The nature of such materials is explained in "Polymer Science and Materials", Tobolsky, A. V. M. and Mark, H. F., Wiley-Interscience 1971.

The poly(ethylene oxide) based polyurethaneurea hydrogels can be used in combination with poly(acrylic acids) or poly(methacrylic acids) to produce pH responsive hydrogels through the formation of macromolecular, hydrogen-bonded association complexes between the polyether and the polyacid segments within the hydrogel structures. These materials are soluble in solvent systems and are therefore suitable for the production of pH responsive hydrogel films and coatings. It has been demonstrated that the PUU/polyacid complexed membranes have a low to high swelling response at about pH4.0 in citrate/phosphate buffer systems over the range pH2.2-pH8.0.

The swelling behavior of poly(acrylamide-co-acrylic acid) copolymer gels in response to changes in ionic strength and pH, indicate that swelling responses can also occur in environments of different ionic strengths and at both low and high pH values. At very low pH the poly(acrylamide-co-acrylic acid) gel will deswell to the volume of an unionised gel. As the pH is increased the gel will increase in swelling as the acid groups become ionised until at high pH values, (>pH10), the gel begins to deswell due to the increased concentration of cations within the gel. It has been shown that the PUU/polyacid hydrogels display this type of swelling response at high pH values(pH10-pH12).

A further group of hydrophilic polymers comprising Polymeric microgels have been developed (UK patent GB2090264B), via a solution polymerisation process, comprising crosslinked particles which are capable of forming a sol in the reaction solvent. These crosslinked particles or microgels can be designed to have specific functionalities, reactivities, solubility and size. Basic poly(methylmethacrylate-co-(dimethylamino)ethylmethacrylate) microgels have been developed which, when incorporated into a PUU hydrogel matrix produce pH responsive hydrogel materials which exhibit a change in swelling at about pH6-7. The versatility of the microgel process means that microgels can be prepared which will respond to any chosen external stimuli. For example, microgels incorporating acidic and/or basic groups will respond to changes in pH and/or ionic strength, poly(hydroxyethylmethacrylate-co-dinitrophenol) microgels will respond to the presence of amines, poly(hydroxyethylmethacrylate-co-azobenzoate) microgels will respond to UV radiation and poly(N,N-alkyl substituted acrylamides) based microgels will have a swelling response in relation to the system temperature.

Microgels can be combined in a two component system with a PUU hydrogel matrix, or a carrier or binder to produce responsive hydrogel materials, which swell or deswell i.e. shrink, on exposure to the specific target.

Another class of preferred hydrogels includes acrylamide based polymers, for example polyacrylamide, poly-n-isopropyl acrylamide, poly-n-methyl acrylamide, poly-n,n-dimethyl acrylamide and their methyacrylamide analogs. It is understood that these polymers my may be essentially homopolymers or may be co-polymers with another hydrophilic or hydrophobic monomer.

Sensor Material Function

Possible hydrogel materials for use with the sensor device of the invention are described above. The ability of the hydrogel to undergo a significant change in volume enhances the sensitivity of the device. The selectivity of the device is obtained via the use of particular receptor components in the sensor material. The function of the sensor material is best described by reference to FIGS. 5, 6 and 7.

A typical sensor material 2 shown in FIG. 5 is comprised of one or more hydrophilic polymers which make up a network of fibrous strands 20 and 21. The strands have some degree of freedom of movement in the aqueous environment of the hydrogel. Although the hydrogel contains large numbers of strands only two are shown here to simplify the description. The strands are bound to receptors which here are single stranded DNA sequences 22 and 23. A single stranded sequence will bind to its complementary sequence.

A complimentary single-stranded DNA target sequence 24 is added as shown in FIG. 6. Half of the target sequence 26 is complementary to the receptor sequence 22 and has hybridized to the sequence 22 as shown in FIG. 6.

FIG. 7 shows the other half of the target sequence 24 bound to the receptor sequence 23. This pulls the strands 20 and 21 together and thereby compresses the volume of the sensing material 2. In practice there may be a plurality of receptors distributed throughout the sensing material 2 and a plurality of target sequences added. There may be tens, hundreds, thousands or more receptor sequences and similar numbers of target sequences.

It is known that homologous sequences hybridize to each other. The hybridization conditions such as the pH and temperature can be varied as needed, e.g. to allow hybridization only with an exact match or with a sequence with 90% or more or 95% or more or 99% or more homology. Conditions for the binding of other pairs such as antibodies to epitopes can also be varied to obtain desired results in terms of selectivity.

The nucleotide sequences may be sequences corresponding to those found in abnormal cells, e.g. cancer cells, and the antibody may be those that bind to epitopes on the surface of pathogenic bacteria or viruses.

It is understood that peptide nucleic acid sequences (PNA) or RNA may be used in place of DNA in the sensor.

Techniques for obtaining and placing receptors in or onto the sensor material are generally conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Wei & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction* (Mullis et al., eds., 1994); *Current Protocols in Immunology* (J. E. Coligan et al., eds., 1991); *Short Protocols in Molecular Biology* (Wiley & Sons, 1999).

Antibodies which bind to pathogenic bacteria and/or antigens or epitopes of such bacteria can be used as the receptor in or on the sensor material. Pathogenic strains of *E. Coli* and/or *Salmonella* are typical. The receptor could be a wide variety of *Salmonella*, including any of the known groups, species or strains, more preferably groups A, B, or D, which includes most species which are specific pathogens of particular vertebrate hosts. Illustrative of the *Salmonella*-causing disease for which live vaccines can be produced are *S. typhimurium; S. enteritidis, S. typhi; S. abortus-ovi; S. abortusequi; S. dublin; S. gallinarum; S. pullorum*; as well as others which are known or may be discovered to cause infections in mammals.

Other organisms for which and their antibodies which could be used as receptors include *Yersinia* spp., particularly *Y. pestis, Vibrio* spp., particularly *V. cholerae, Shigella* spp., particularly *S. flexneri* and *S. sonnei; Haemophilus* spp., particularly *H. influenzae*, more particularly type b; *Bordetella*, particularly *B. pertussis; Neisseria*, particularly *N. meningitidis* and N. gonorrhoeae; *Pasteurella*, particularly *P. multocida*, pathogenic *E. coli*, and *Treponema* such as *T. pallidum*; as well as others which are known or may be discovered to cause infections in mammals.

Other pathogenic bacteria are known in the art and include, for example, *Bacillus*, particularly *B. cereus* and *B. anthracis; Clostridium*, particularly *C. tetani, C. botulinum, C. perfringens*, and *C. difficile; Corynebacterium*, particularly *C. diphtheriae; Propionibacterium*, particularly *P. acnes; Listeria*, particularly *L. monocytogenes; Erysipelothrix*, particularly *E. rhusiopathiae; Rothia*, particularly *R. dentocariosa; Kurthia; Oerskovia; Staphylococcus*, particularly *S. aureus, S. epidermidis*, and *S. saprophyticus; Streptococci*, particularly *S. pyogenes, S. agalactiae, S. faecalis, S. faecium, S. bovis, S. equinus*, and *S. pneumoniae; Klebsiella*, particularly *K. pneumoniae; Enterobacter*, particularly *E. aerogenes; Serratia; Proteus*, particularly *P. mirabilis; Morganella*, particularly *M. morganii; Providencia; Pseudomonas*, particularly *P. aeruginosa; Acinetobacter*, particularly *A. calcoaceticus; Achromobacter*, particularly *A. xylosoxidans; Alcaligenes; Capnocytophaga; Cardiobacterium*; particularly *C. hominis; Chromobacterium*; DF-2 Bacteria; *Eikenella*, particularly *E. corrodens; Flavobacterium; Kingella*, particularly *K. kingae; Moraxella; Aeromonas*, particularly *A. hydrophila; Plesiomonas*, particularly *P. shigelloides; Campylobacter*, particularly *C. jejuni, C. fetus* subspecies fetus, *C. coli, C. laridis, C. cinaedi, C. hyointestinalis*, and *C. fennelliae; Brucella*, particularly *B. melitensis, B. suis, B. abortus*, and *B. canis; Francisella*, particularly *F. tularensis; Bacteroides*, particularly *B. fragilis* and *B. melaminogenicus; Fusobacteria; Veillonella; Peptostreptococcus; Actinomyces*, particularly *A. israelii; Lactobacillus; Eubacterium; Bifidobacterium; Arachnia; Legionella*, particularly *L. pneumophila; Gardnerella*, particularly *G. vaginalis; Mobiluncus; Streptobacillus*, particularly *S. moniliformis; Bartonella*, particularly *B. bacilliformis; Calymmatobacterium*, particularly *C. granulomatis; Mycoplasma*, particularly *M. pneumoniae* and *M. hominis; Mycobacterium*, particularly *M. tuberculosis* and *M. leprae; Borrelia*, particularly *B. recurrentis; Leptospira*, particularly *L. interrogans; Spirillum*, particular *S. minor; Rickettsiae*, particularly *R. rickettsii, R. conorii, R tsutsugamushi*, and *R. akari; Chlamydiae*, particularly *C. psittaci* and *C. trachomatis*.

The sensing material may be almost pure nucleotide e.g. DNA or 90% or more or 95% or more DNA. Further in this and other embodiments the target molecule amplifies the change in volume. For example, one unit volume of target molecule causes a 5 or more, 10 or more, 20 or more unit in volume change (expansion or reduction).

Collapsible Polymer

Polymers may exhibit Van Der Waals forces. These forces are interatomic or intermolecular forces of attraction. The forces are due to the interaction between fluctuating dipole moments associated with molecules not possessing permanent dipole moments. These dipoles result from momentary dissymmetry in the positive and negative charges of the atom or molecule, and on neighboring atoms or molecules. These dipoles tend to align in anti-parallel direction and thus result in a net attractive force. This force varies inversely as the seventh power of the distance between charged areas such as ions.

As indicated above the Van Der Waals forces are due to interaction between fluctuating dipole moments associated with molecules which do not possess a permanent dipole moment. Thus, hydrogels can be prepared from a monomer or group of monomers that have both a hydrophobic and a hydrophilic group. The hydrogel may be in a normal hydrated state in a first environment which could be in pure water due to the arrangement of the different hydrophobic and hydrophilic groups the hydrogel will exhibit an upper critical solution temperature. This critical solution temperature means that as the temperature is increased the polymer will become less soluble. At a given temperature the polymer will collapse. For example, at about 37° Centigrade the polymer n-isopropyl acrylamide will collapse. The polymer collapses at the point where the Van Der Weals interactions of the hydrophobic groups on the polymer formed overcome the Van Der Weals and hydrogen bonding of the water and the polar hydrophilic portion of the polymer. Thus, with the n-isopropyl acrylamide polymer the collapse will occur at the point where the Van Der Waals interactions of the hydrophobic n-isopropyl groups overcome the Van Der Weals and hydrogen bonding of the water and polar acrylamide portion of the hydrogen bond. At this point the hydrophobic chains of the polymer attract each other and form a relatively tight coil structure. Those skilled in the art reading this disclosure will understand that such polymers comprised of different proportional amounts of hydrophobic and hydrophilic groups can be used to sense a chemical species within the water. For example, it is possible to detect a hydrophobic chemical species in the water due to the effect of these species on the temperature at which the polymer will collapse. The polymer can be designed to collapse at a particular temperature in pure water. Thus, if the polymer does not collapse at that temperature a chemical species is known to be present in the water.

Those skilled in the art will recognize that polymers of the type described above can be used in a variety of different ways as sensors. It is not necessary for the polymer to "collapse" but merely change volume such as by contracting or swelling. It is possible to determine the initial volume of the polymer gel in the absence of a chemical of interest and then monitor the volume of the polymer gel in the presence of that chemical of interest. If the chemical of interest or analyte is hydrophobic, it will associate with hydrophobic portions of the hydrogel thereby increasing the Van Der Waals attractive forces and having an effect on the gel which will cause the gel to contract or swell as when in water.

It is possible to measure the UCST of a gel in a first environment (for example pure water), and then monitor the USCT of the gel in the presence of a particular chemical (analyte species) to be detected. The UCST can be measured conveniently by measuring the volume of the hydrogel as a function of temperature. This measurement can be carried out, for example, using a Piezoresistive Microcantilever. Alternatively, the measurement can be carried out by measuring the heat flow of the sample as a function of temperature such as by using a differential scanning calorimeter.

Phase Change Crystallizable Polymers

Polymers exhibiting well defined first order phase changes (melting and crystallization) are advantageously used because they undergo an abrupt change in one or more of viscosity and volume due to specific volume changes associated with the melting and freezing transition. Examples of crystalline polymers include polyethylene, polypropylene, co-polymers of ethylene and secondary monomers including without limitation vinyl acetate, ethyl acrylate, methacrylate, acrylic acid, propylene, higher alpha olefins, co-polymers of propylene, polytetrahydrofuran, polyethylene adipate, and its homologs and analogs and other known crystalline or semi-crystalline polymer which may be found for example in the Polymer Handbook, Fourth Edition, 1999, Section VI pages 1 to 192, Wiley Interscience Publications. In one embodiment, the polymer is a crystalline material with a phase transition point between 10° C. and 110° C. Crystalline polymers used in this invention preferably have a change in volume upon melting of at least 2%, preferably at least 5%, and most preferably at least 7%. Volume change upon melting is readily measured via dilatometry or by measuring specific gravity above and below the melting point. It is also desirable that the polymer exhibit a melting point at a temperature that is convenient for measuring, for example from about −20° C. to about 150° C., preferably, from about 5° C. to 80° C. and more preferable from about 20° C. to about 60° C. While these temperatures are preferable for use in aqueous systems they are not meant to limit the range of polymers that may be used for specific applications where higher or lower melting ranges may be desirable.

A preferred phase change crystalline polymer is a side chain crystallizable polymer. Examples of side chain crystallizable polymers and their synthesis are described in U.S. Pat. No. 5,120,349, U.S. Pat. No. 4,830,855, U.S. Pat. No. 5,665,882 and U.S. Pat. No. 5,783,332 and within the "Journal of Polymer Science": Macromolecule Reviews (1974) 8:117 and "Journal of Polymer Science": Polymer Chemistry Addition (1981) 19:1871-1873. Side-chain crystallizable polymers are sometimes referred to as "comblike" polymers and are available commercially. These polymers are generally reviewed in the "Macromolecular Review" article referred to above.

Side-chain crystallizable polymers used in the present invention have the following general structural formula:

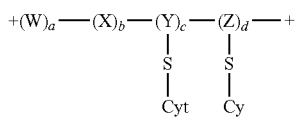

wherein W and X are each respectively a first and a second monomer unit, which monomer unit may be any molecular moiety connectable to an adjoining molecular moiety (i.e., polymerizable), Y and Z are each independently a backbone monomer unit which may be any molecular moiety or atom, each S is independently a linking group or spacer unit and is optionally present, Cyt and Cy are each independently a crystallizable moiety connected to the respective backbone directly or via the spacer unit, and a, b, c, d and e are each, independently, integers ranging from 0-1,000 with the proviso that all are not zero so that sufficient Cyt and Cy are present so as to provide a Mw which is equal to or greater than twice the sum of the Mws of W, X, Y and Z, and further wherein the polymers have a heat of fusion (ΔHf) of at least five joules/gram, and preferably about ten joules/gram. It is understood that when the variables a, b, c and d are greater than 1, the monomer units W, X, Y and Z can be repeating units or a mixture of different monomer units. For example, if "a" is 100, W could be a mixture of styrene, vinyl acetate, acrylic acid, methyl styrene and hexadecyl acrylate in ratios of 5:5:2:5:83. Thus, any of the monomer units W, X, Y and Z can be mixtures of polymerizable monomers.

The polymer may if desired contain polar groups to modify solubility characteristics, enhance specific binding, for example the additions of a carboxylic acid from acrylic acid will produce a polymer having an increased binding capacity and selectivity for amines. Additionally the polymer may have chemically attached antibodies, DNA sequences, ion specific ligands, or other receptor sites designed to enhance sensitivity or selectivity toward one or more analyte.

The backbone of the polymer (defined by W, X, Y and Z) may be any organic structure (aliphatic or aromatic hydrocarbon, ester, ether, amide, etc.) or an inorganic structure (sulfide, phosphazine, silicone, etc.). The spacer linkages can be any suitable organic or inorganic unit, for example ester, amide hydrocarbon, phenyl, ether, or ionic salt (for example a carboxylalkyl ammonium or sulfonium or phosphonium ion pair or other known ionic salt pair). The side-chains (defined by S, Cyt and Cy) may be aliphatic or aromatic or a combination of aliphatic side-chains of at least 10 carbon atoms, fluorinated aliphatic side-chains containing at least 6 carbons, and alkyl styrene side-chains wherein the alkyl contains from 8 to 24 carbon atoms.

The length of any side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene, the side chain can be as little as 2 times the length as the distance between branches. In any case, the side-chain units (generally 10-30 carbons and preferably 12 to 18 carbons in length) should make up greater than 50% of the volume of the polymer, preferably greater than 65% of the volume. Co-monomers added to a side-chain polymer usually have an adverse effect on crystallinity. Small amounts of various co-monomers can be tolerated, usually up to 10 to 25 volume percent.

Crystalline polymers, including side chain crystalline polymers have been found to have a melting point or range that is highly sensitive to the presence of added chemicals. Thus, a side chain crystalline polymer that melts at 48° C. when purified, for example polyoctadecyl acrylate will melt at a significantly lower temperature when it contains (has dissolved or molecularly dispersed within it) a small-amount of organic chemical, for example toluene or heptane.

Thermal Properties of Osmotically Responsive Hydrogels

In yet another aspect of the invention it has been shown that there is a strong correlation between osmolality and the thermal properties of osmotic responsive hydrogels of the type described herein. For example, higher osmolality solutions result in polymers having a lower heal capacity and a lower peak and onset temperature.

Thermosensitive hydrogels have been well documented in the literature due to their applicability as microactuators. Hydrogel thermosensitivity is evidenced by a sudden decrease in the degree of swelling at a given temperature. This phenomenon has been attributed to a thermally-induced collapse of the hydrogel from an extended coil into a globular structure (D. Kuckling, et al. Polymer Bulletin 2000, 44, 269). The temperature at which this occurs is called the lower critical solution temperature (LCST). The LCST is actually a phase transition, which involves endothermic heat energy transfer similar to the heat of fusion during melting of a substance.

Differential scanning calorimetry (DSC) has been identified as a convenient method for determining the LCST of swollen hydrogels. Small hydrated samples of the gels are prepared in hermetically sealed pans and then are placed in the DSC cell for ramping through the temperature range of interest. A plot is obtained that shows thermal events as a function of temperature. A large endothermic peak appears which corresponds to the heat capacity change during the phase transition from a fully swollen to collapsed gel. This thermal event occurs well below the boiling point of water in the gel solution.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Hydrogel Polymer

Polymer is prepared comprising hydroxypropyl acrylate having a MW of between 200,000 and 500,000 daltons. The resulting polymer is washed with ethyl actetate to remove residual monomer and taken up in a 1:1 mixture of ethyl acetate: tetrahydrofuran at 25% solids.

To a 3 gram polymer solids sample is added 0.2% w/w PFAZ 233 polyfunctional crosslinking agent (BAYER) and cast onto glass Petri dishes. The polymer is allowed to crosslink and dried at 90° C. for 12 hours.

The water uptake of the polymer is measured at varying osmolalities and seen to be highly responsive to changes in osmotic properties. Further details regarding hydrogel polymers are provided below in Example 8.

Example 2

Osmolality Sensor

Polymer solution as above is diluted to 10% solids and a 1.0 mm thick glass chip is dip coated with the solution and dried. The resulting polymer film is approximately 25 microns thick. A piezoresistive microcantilever (Veeco) (and it's electrical contacts including solder wires) is dip coated with a 10% solids solution of 2 part epoxy twice and dried at 90° C. The cantilver is then mounted proximate to the glass chip such that the cantilever is just touching the surface of the polymer. The resulting assembly is dip coated a second time to embed the cantilever.

The sensor responds predictably to changes in osmolality in the range of interest for human saliva (50-200 mOsmol). Further details on such a sensor are provided below in Example 8.

Example 3 pH Sensor

A polymer is prepared by polymerizing:

85 g hydroxy propyl acryate 13 g ethyl hexyl acrylate 2 g acrylic acid

The resulting polymer is purified and taken up in ethyl acetate.

A sensor is made as described in Examples 1 and 2 and responds to pH over the range of 5 to 9. The most dramatic response is seen between pH 7 and 9 and corresponds to an abrupt solubility change.

A second pH responsive polymer was prepared using hydroxy-ethyl-methacrylate and acrylic acid. Upon crosslinking this polymer showed an abrupt increase in swelling starting at pH 5 and ending by pH 6.5.

Example 4

Small Pox Virus Detector

A polymer is prepared in DMF as solvent from

N-isopropy acrylamide (98)

Acrylic acid (0.5)

N-hydroxyxuccinimide methacrylate (NHSI) (1.5)

The resulting polymer is taken up in water and allowed to react with small pox monoclonal antibodies. Excess NHSI groups are reacted with methyl amine.

Polymer is applied to a sensor and crosslinked using Xama 7 (Bayer) and equilibrated in pH 7.5 buffer. Introduction of deactivated small pox virus or vaccinia analog causes an abrupt reduction in hydrogel volume and subsequent cantilever resistance change.

Example 5

DNA Sensor

Polymer prepared as in Example 4 and then reacted with amino functional single strand DNA segment.

The sensor selectively responds to the complimentary DNA strand.

Example 6

Ion Selective Sensor

Polymer is prepared from n-isopropyl acrylamide and 4-acrylamidobenzo 18-crown-6 ether and acrylic acid. This sensor is selectively responsive for cations such as lead and is selective for potassium over sodium.

Example 7

Solvent Sensor

A polymer is prepared by polymerization in butyl acetate of:
Octadecyl acrylate (95)
Acrylic Acid (5)

Resulting polymer is solvent cast with 0.2% hexamethylene diisocyanate crosslinking agent to make a microcantilever sensor. The sensor device has a thermistor and heating element such that the sensor is maintained at 45° C. The sensor responds to toluene vapor 10 times more sensitively than a comparable sensor maintained at 25° C. The increased sensitivity is due to the ability of low levels of toluene to depress the melting point of the polymer thus inducing a phase change and subsequent volume expansion.

Example 8

Osmolality Sensing Polymers

Another embodiment of the invention provides a non-invasive dehydration sensor designed for intraoral attachment (e.g. attached to gum, teeth or cheek) capable of monitoring changes in saliva osmolality as water is lost by the tissues. The sensing material polymer swells in saliva mimicking solutions of low osmolality (representing fully hydrated oral fluids), and shrinks significantly in response to small osmolality increases at the onset of body dehydration. Literature searches revealed that the relevant saliva osmolality range for fully hydrated and dehydrated individuals is between 50-200 mOsm. Sensor materials preferably have the following characteristics:

Strong osmotic swelling response
Stable for extended times in aqueous media of low osmolality
Solution processable (dip coat, spin coat, etc.)
Bond to silicon, glass, aluminum, ceramic
Does not crack when dried
Safe, non-toxic and inert.

Specific materials with these characteristics include forms of the following polymers: Polymers and Co-polymers of Vinyl Acetate; Vinyl Acetate Homopolymer; Vinyl Acetate/ Vinyl Propionate; Ethylene/Vinyl Acetate; Vinyl Acetate/ Acrylic Ester; Co-polymers of Vinyl Alcohol/Ethylene; Hydrophilic Thermoplastic Polyurethanes; and Acrylic Hydrogels Testing Commercially Available Polymer Candidates Other polymers can be tested for suitability with a test involving gravimetric measurement of polymer weight gain as function of immersion time in aqueous media of "zero" and hypertonic osmolalities. To pass the screening test, a polymer film should exhibit a robust swelling difference between immersion in DI water (0 Osm/Kg) and 4% NaCl solution (~1.3 Osm/Kg). Results of our initial screening test are shown in Table 1.

TABLE 1

Osmotic Response Results of Commercial Hydrophilic Polymers

| Polymer | Composition | Swelling Ratio DI water:4% NaCl | Pass/Fail | Justification (Comment) |
|---|---|---|---|---|
| PVAc | Polyvinylacetate | 2.5 | Fail | Tg = 45 C. |
| Flexbond 325 | PVAc-co-butyl acrylate | 3.1 | Fail | Low Ratio |
| Airflex 500 | PVAc-co-ethylene | 6.8 | Pass | Problem with Poor Adhesion |
| Airflex EF811 | PVAc-co-ethylene | 9.8 | Fail | Fell apart |
| EVAL L171A | Ethylene vinyl alcohol co-polymer | 1.1 | Fail | Low Ratio |
| Estane 58245 | Polyurethane | 1.1 | Fail | Low Ratio |

As shown, the Airflex (PVAc-co-ethylene) polymers exhibited the highest swelling ratios. However, the Airflex EF811 failed because the films degraded in response to high swelling. The Airflex 500 passed, but exhibited poor adhesion during high swelling, which suggested degradation of the material. Thus, these candidates failed the overall design criteria for our sensing polymer application.

The test results for the series of commercial polymers led to the following conclusions:

Swelling is related to polymer polarity
Swelling ratio is not readily predictable based on structure
High swelling generally leads to poor bonding
Swelling response is fast and can be increased with thin films.

Hydrogel-type polymers were examined as osmolality sensing materials. The osmotic swelling response of a crosslinked polyacrylamide (Soil Moist) in DI water and 4% NaCl test solutions was tested. This polymer afforded a very dramatic swelling ratio of 12.

Figure 8:
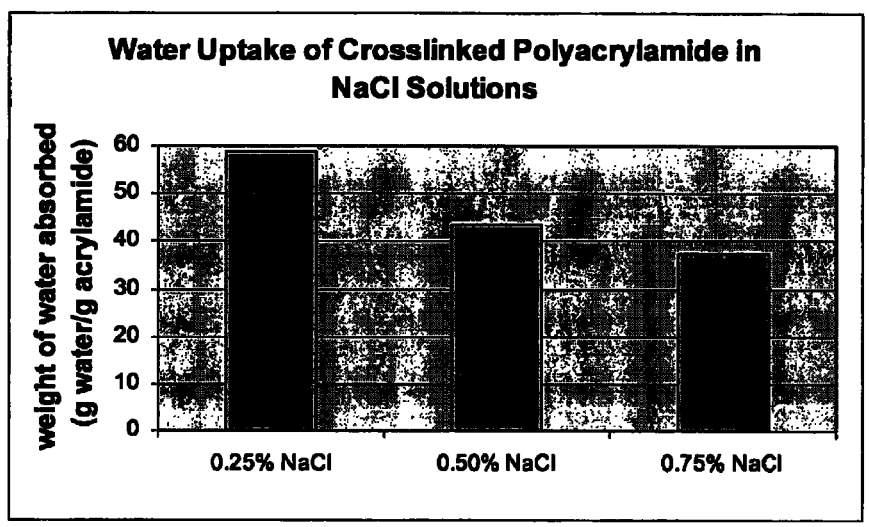
FIG. 8 is a bar graph showing the water uptake of crosslinked polyacrylamide in three different sodium chloride solutions.

To test the response at biologically relevant osmolalities, dry polyacrylamide was immersed in series of hypotonic solutions and water absorption was measured at equilibrium. FIG. 8 shows the swelling differences observed in solutions having NaCl concentrations of 0.25-, 0.5-, and 0.75% (corresponding to hypotonic osmolalities 85-, 171-, and 256 mOsm/Kg). As shown, the polyacrylamide material exhibited large swelling differences for each small incremental concentration change.

This swelling behavior met criteria for robust osmolality response. However, the raw material must be soluble/processable for casting a polymer film on silicon substrates during device fabrication. These criteria were not met by current commercial crosslinked polyacrylamides, such as Soil Moist. Thus, it was necessary to design custom hydrogel prepolymers that could be easily processed into thin films, followed by a crosslinking reaction step in-situ.

Custom Designed Hydrogels as Osmolality Sensors

Acrylamide (AM) based hydrogel polymers appeared to be very promising for the hydration sensor application due to:
High absolute swelling ratio
Strong osmotic response
Extensive research findings published in the literature
Ability to copolymerize with a wide range of co-monomers for tailoring properties.

Polyacrylamide (PAM) films that are uncrosslinked, or which lack significant amounts of phase separated hydrophobic blocks, will dissolve and lose mechanical integrity in aqueous solutions. For this reason, none of the commercially available PAMs (i.e. for electrophoresis gel preparation) gave preferred results. Consequently, a series of resins with varying amounts of hydrophilic character were prepared. These are listed as follow:
1. Polymethacrylamide-co-methacrylic acid (PMAM-co-MAA) (99:1 and 98:2% w/w)
2. Ethylhexyl acrylate-co-acrylamide (EHA-co-AM) (80:20, 70:30 and 45:55% w/w) (each with low levels of acrylic acid)

These PAMs have the ability to undergo latent crosslinking after casting a film by adding a commercial crosslinking agent, such as Xama 2 (Bayer Corp.) that reacts with the carboxylic acid groups in the polymer as the film dries.

Synthesis and Characterization of PMAM-co-MAA Hydrogels

The PMAM-co-MAA hydrogel precursors were successfully synthesized and purified. These materials were cast into films from aqueous solutions containing the crosslink agent, Zinplex 15, which reacted with carboxyl groups as the film dried. The resulting films were brittle and cracked when dried completely. Some films were left partially hydrated to avoid cracking, and were then immersed in aqueous solutions to test for swelling. Visible swelling occurred, but the gels failed to maintain dimensional stability and much of the material dissolved. Thus, the PMAM-co-MAA materials were not preferred for sensor materials.

Synthesis and Characterization of EHA-co-AM Hydrogels

Synthesis of the EHA-co-AM hydrogel precursors revealed that high AM monomer content (i.e. 45% w/w) resulted in some polymer precipitation during polymerization in ethyl acetate:ethanol (60:40). However, two EHA copolymers that contained lower AM levels (20- and 30% w/w) were successfully prepared. In the case of the 30% AM copolymer, the solubility during reaction was ensured by using DMAc as the co-solvent with ethyl acetate (25:75).

Figure 9:
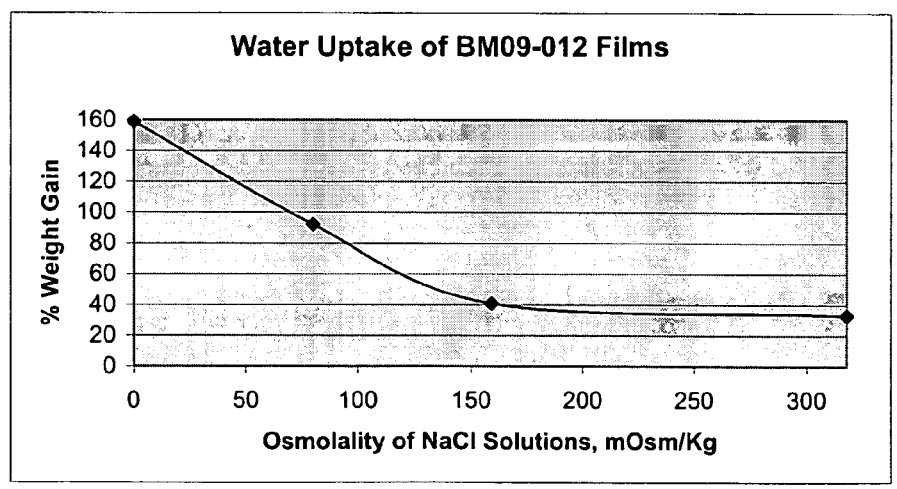
FIG. 9 is a graph showing the water uptake in percentage of weight gain versus osmolality of sodium chloride solutions.

The osmotic response of these two copolymers was characterized using a series of hypotonic (0.1 to 0.75% w/v) and hypertonic (1- and 4% w/w) NaCl solutions. Results indicated that the EHA-co-AM (30% AM, BM09-012) was the most promising candidate because it afforded a rapid and reproducible response, while resisting cracking/delaminating. FIG. 9 shows the equilibrium water absorbance of the films plotted as a function of osmolality for a series of NaCl solutions. As shown, these films exhibited a large swelling difference as osmolality increased/decreased within the range of biological interest (50-200 mOsm). However, some polymer dissolved in test solutions during extended immersion, especially at low osmolalities.

Attempts were made to optimize the stability of BM09-012 by purifying the prepolymer using fractional precipitation/washing, and then adding Xama 2 to prepare crosslinked films. The osmolality responses of the modified polymer films were comparable to those of the unmodified version. However, the films remained unstable at low osmolality.

The properties of EHA-co-AM hydrogel precursors can be improved by designing polymerization conditions that afford better control of the distribution of hydrophilic-hydrophobic monomer units, while optimizing molecular weight. Additionally, it is possible to optimize the ratio and type of crosslinking agent for affording osmotically-sensitive hydrogels that remain stable at low osmolality.

Synthesis and Characterization of Hydrogels Based on Hydroxypropyl Acrylate.

Osmotically sensitive hydrogels were designed based on an alternate hydrophilic acrylic monomer, 1-hydroxypropyl acrylate (HPA, Rocryl 430-Rohm and Haas). A series of HPA-based polymers containing different weight percents of HPA (shown in Table 2) were successfully prepared.

HPA monomer contains an acrylic acid side product, which can furnish up to 1% w/w carboxyl groups in an HPA homopolymer. The low levels of carboxyl groups in our HPA hydrogel prepolymers provided crosslinking sites for the reactive polyfunctional aziridine (Xama 2, and PFAZ 322).

In some cases, diphenylmethane diisocyanate (MDI) was used as a crosslinking agent. It preferentially reacts with the —OH groups of HPA, but can still crosslink low levels of carboxyl groups.

TABLE 2

Osmotic Response Results of HPA-based Hydrogels

| Polymer | Composition | Crosslinking Agent | Swelling Ratio 0.25%:1.0% NaCl | Evaluation/ Comments |
|---|---|---|---|---|
| BM09-014 | HPA-co-EHA 60:40 | Xama 2 (0.05% w/w) | 8.8 | Good Osmotic Response/Large Sol Fraction |
| BM09-015 | HPA-co-EHA 50:50 | MDI (0.25% w/w) | 1.0 | Low Osmotic Response/Low Water Absorption |
| BM09-019 | HPA-co-EHA 75:25 | MDI (0.25% w/w) | 1.6 | Pre-soak for Good Osmotic Response |
| BM09-032 | HPA homopolymer | PFAZ 322 (0.77% w/w) | 1.4 | Good Osmotic Response (No Presoak) |

TABLE 2-continued

Osmotic Response Results of HPA-based Hydrogels

| Polymer | Composition | Crosslinking Agent | Swelling Ratio 0.25%:1.0% NaCl | Evaluation/ Comments |
|---------|-------------|--------------------|--------------------------------|----------------------|

Osmotic swelling responses of these HPA-based hydrogels were evaluated using a series of NaCl solutions of the following concentrations/osmolalities:
 0.1% NaCl, ~34.2 mOsm
 0.25% NaCl, ~85.5 mOsm
 0.5% NaCl, ~171 mOsm
 1% NaCl, ~342 mOsm As before, a large measurable swelling difference was desired between low and high osmolalities. For screening, the swelling ratios in 0.25% and 1% NaCl concentrations were measured, and are shown in Table 2. The BM09-014 polymer (60% HPA) exhibited a high swelling ratio of 8.8 between the two test solutions. However, another test sample that was immersed in a 0.1% NaCl solution lost ~80% of its original dry weight. Since the polymer was not completely "gelled" by the crosslinking reaction, a large fraction of "sol" polymer had dissolved. This indicates that the level of crosslinker may be increased to provide higher gel content and a more stable structure.

The BM09-019 polymer (75% HPA) exhibited measurable and reproducible swelling responses within the desired osmolality range. However, this was not achieved until after the dry films had been "conditioned" by pre-soaking in deionized water pH 8. As mentioned above, HPA polymers contain low levels of carboxyl groups. Although some of the acidic groups have been consumed by reacting with MDI or Xama crosslinkers, the polymers still contain some free unreacted carboxyls. At high pH, these are expected to deprotonate to form the carboxylate anion. The carboxylate functionalities increase water affinity of the polymer and, consequently, higher swelling occurs at low osmolalities.

Figure 10:
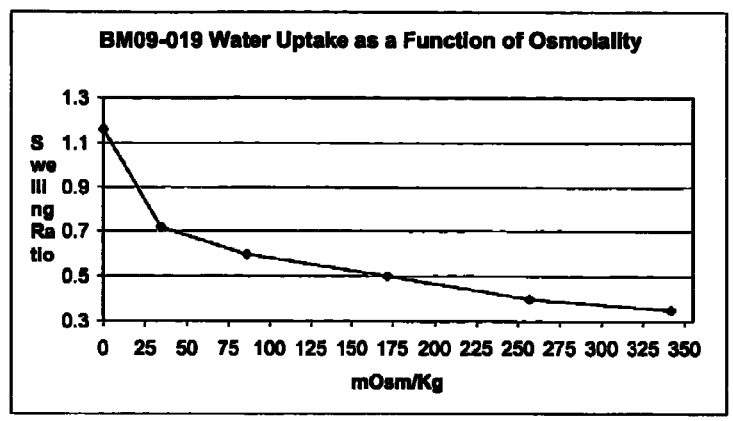
FIG. 10 is a graph showing water uptake as a function of osmolality.
Figure 11:
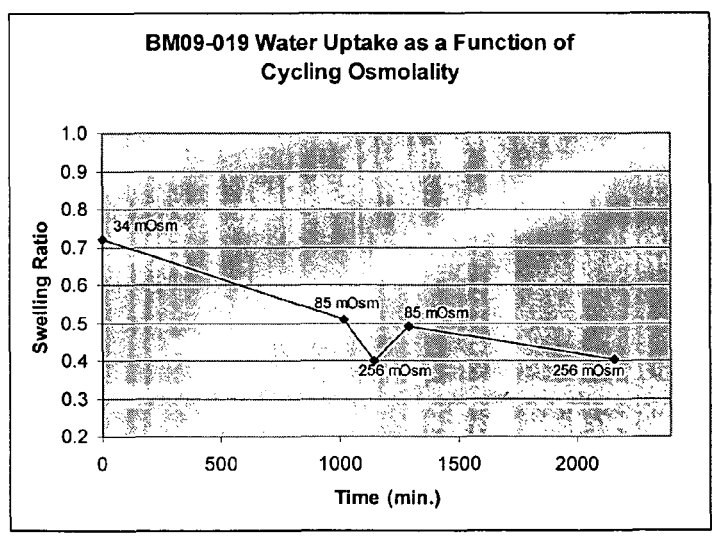
FIG. 11 is a graph of the swelling versus time.

Osmotic swelling responses of "conditioned" BM90-019 films are shown in FIG. 10. The gel (crosslink) content of this system was sufficient to prevent large amounts of material from dissolving at low osmolalities. Additionally, the swelling response was reproducible when cycling between low osmolality concentrations, as shown in FIG. 11. The osmolal test solutions were buffered to pH 8 for these measurements. Future studies will involve testing osmolality response in solutions buffered to within the pH range of human saliva (6-7).

The polymer BM09-015 (50% HPA) did not differ in swelling response as a function of osmolality. The results show that the combination of high crosslink density and lower HPA content prevented high water uptake and swelling. To obtain better responses, the films were "conditioned" in deionized water at pH 8. However, following treatment, the maximum water absorption throughout the osmolality/pH 8 testing series was less than 20% w/w, and osmotic selectivity was still not achieved. Thus, this polymer is not preferred in terms of design criteria for osmotic selection.

To achieve better osmotic response and eliminate the need for a film "conditioning" step, an HPA homopolymer (BM09-032) was prepared and characterized. The hydrophilic monomer content of 100% was expected to increase the rate and amount of water absorption, without compromising osmotic selectivity. Additionally, it was believed that the crosslink density could be increased without decreasing the water absorption of the polymer. It was anticipated that higher gel content would prevent excessive dissolving of polymer during immersion in solutions of low osmolality.

Figure 12:
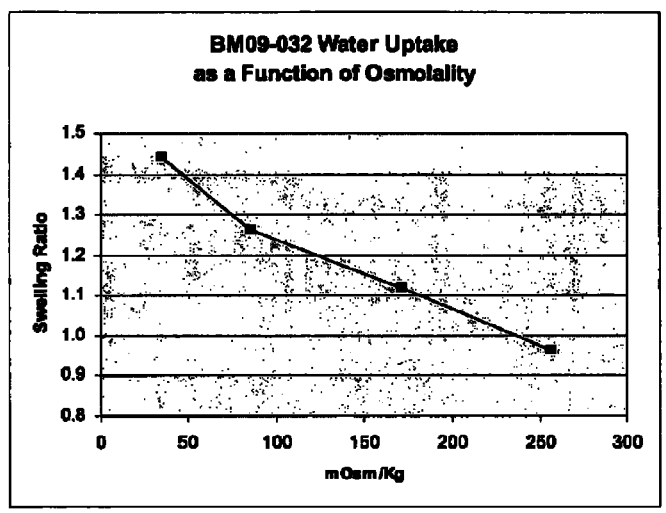
FIG. 12 is a graph of the swelling versus osmolality.
Figure 13:
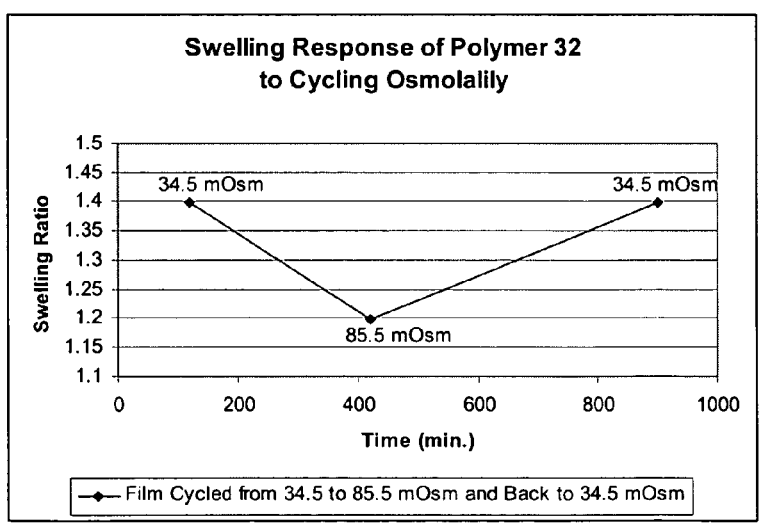
FIG. 13 is a graph of the swelling ratio versus time.

MDI-crosslinked films of BM09-032 were screened using the osmolality/pH 8 series of solutions. As shown in FIGS. 12 and 13, there were significant swelling differences observed during cycling between low and high osmolalities.

Figure 14:
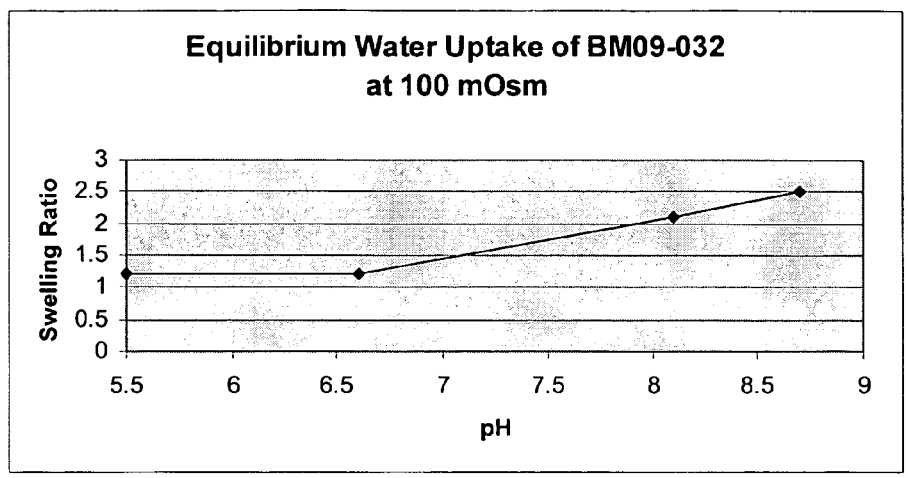
FIG. 14 is a graph of the swelling ratio versus pH.

Studies of osmotic swelling at different pH levels were conducted to ascertain any differences within the range of human saliva. Saliva mimic solutions (~100 mOsm) buffered to the lower pH levels of biological interest were used, and 100 mOsm solutions with pH>8 were used for comparison. The equilibrium water absorbance of the HPA homopolymer has been plotted as a function of pH in FIG. 14.

As expected, the water absorbance (swelling) was significantly higher at pH>7. This can be attributed to the higher levels of carboxylate that form when the basicity of the solution increases. This polymer can be tested in a series of saliva mimic solutions encompassing the relevant pH and osmolality ranges found in fully hydrated and dehydrated individuals. Another option is to fully purify the HPA monomer before synthesizing the polymer. Removal of the acrylic acid impurity before making polymer would result in eliminating pH sensitivity because the carboxyl groups would be eliminated.

Osmolality testing/screening results indicated that HPA-based hydrogels were the most promising in terms of sensitive and reproducible response, especially over long soak times. The HPA homopolymer (BM09-032) was preferred as an osmolality sensing polymer for the following reasons:
 Uncomplicated synthesis technique
 Simple purification procedure
 Soluble, processable from low boiling point, environmentally-friendly solvents
 Bonds well to glass, and silicon
 Affords high level of crosslinking, with no visible cracking
 Osmotically sensitive without conditioning/purification steps
 Fast and reproducible response
 Stable for extended times in aqueous media of low osmolality.

A dip coating method was developed for incorporating the BM09-032 into the microcantilever sensor device. Swelling data based on resistance changes during osmolality cycling experiments has been obtained.

Example 9

Polymer Formula for Osmotically Responsive Hydrogel

Preparation of Hydrogel Precursor:
A hydrogel precursor was prepared by polymerizing hydroxypropyl acrylate (CAS 25584-83-2, ~97% purity) and acrylamide (CAS 79-06-1, 100% purity) using an 85:15 weight ratio of the respective monomers. A 20% solids reaction solution was prepared by dissolving the specified amounts of hydroxypropyl acrylate and acrylamide monomers in a water/dimethylacetamide solution (70:30) containing a small amount of potassium persulfate as the initiator (0.15% weight per monomer weight). After purging the reaction solution of oxygen, it was heated with stirring at 60° C. for 32 hours. The clear and viscous polymer solution was cooled slowly to room temperature and then was slowly added to excess deionized water that had been heated to just below boiling. The polymer precipitated in the hot water as a swollen rubbery mass. The hot supernatant fluid was decanted and the precipitate was cooled. A clear viscous stock solution of the polymer was prepared by dissolving the precipitate in ethanol/water (94:6).

Preparation of Crosslinked Hydrogels from Precursor:

A crosslinked hydrogel was prepared by adding a water-compatible crosslinking agent that reacted with the hydroxyl groups in the precursor polymer when heated. The agent used was from the hexa(methoxymethyl)melamine family, which is among those commonly used for crosslinking water-borne paints and coatings. A commercially available solution of this type of agent was used to prepare reactive coatings of the hydroxypropyl acrylate/acrylamide precursor polymer.

The reactive crosslinking mixture was prepared by adding 0.1 weight percent of crosslinker solids per weight of polymer solids in the stock solution. This was followed by addition of a small amount of dilute mineral acid (0.1N sulfuric acid). The solution was stable at room temperature until ready for processing. Films were cast by applying the solution to substrates using spin or mechanical techniques. The resulting clear films were baked at 65° C. until solid and the temperature gradually increased to 80-90° C. to complete the curing reaction.

Determination of Osmotic Swelling Response of Hydrogel in Salt Solutions:

Gravimetric Method:

Crosslinked films were prepared as described above using silane-treated glass as the substrate. Dry weights of the films were determined to the nearest 0.1 mg. Then the films were successively immersed in a series of aqueous sodium chloride solutions ranging in osmolality concentration from 48-160 mOs/Kg. The water uptake was monitored sequentially by periodically removing the films, blotting the surfaces and weighing to the nearest 0.1 mg. Duplicate or triplicate immersion trials were conducted at two different temperatures: 25° C. and 37° C.

The average swelling magnitude at each temperature and osmolality was calculated as the weight ratio of swollen gel to original dry film. A representative plot of swelling ratio versus osmolality of the test solutions appears in FIG. 15. As shown, overall swelling was higher at 25° C. than at 37° C. The hydrogel exhibited osmotically responsive behavior, as shown by the marked increase in swelling ratio as osmolality decreased at the respective testing temperatures. The osmotic sensitivity index at each temperature is calculated as the ratio of swelling at 48 mOsm/Kg to that at 160 mOsm/Kg. The comparable values will indicate that the hydrogel is equally responsive to the change in salt concentration at both temperatures.

Piezoelectrical Displacement Method:

A thin layer of reactive crosslinking polymer solution (~0.001") was deposited on silane-treated glass or silicon and thermally cured. The cured dry film was placed beneath and in surface contact with a piezoresistive microcantilever. A drop of the reactive polymer solution was deposited at the cantilever tip/film interface to bond the piezoelectric material to the cured film. The device assembly was baked at 80° C. to cure the bondline.

The microcantilever assembly was incorporated in an electronic piezoresistive circuit on chip (MEMS device). This was electrically connected to a digital multimeter and data acquisition system for measuring resistance across the microcantilever. Using the multimeter with real-time digital data collection, the resistance change was monitored as the cantilever was mechanically deflected either up or down from its baseline position. Dimensional changes in the hydrogel film beneath the microcantilever occurred as a function of its osmotic swelling in salt solutions. This caused the mechanical deflection of the cantilever, which was measured as a shift in the baseline resistance value.

For the osmotic tests, the cantilever/polymer assembly was first immersed in a salt (sodium chloride) solution of 360 mOsm/Kg concentration and the resistance was allowed to come to a steady state. The osmolality concentration of the original solution was then systematically changed by successive dilution to determine the osmotic swelling response of the hydrogel via resistance change. The osmolality was changed in situ using predetermined volumes of deionized water, which were added dropwise with mixing to the test chamber. The temperature of the chamber was controlled to 25° C. using a refrigerated constant temperature water bath. After each programmed dilution, the resistance response was allowed to come to steady state.

FIG. 16 shows a plot of steady state resistance values measured at each successive osmolality. As shown, the resistance change was inversely proportional to the concentration. At lower osmolality, hydrogel water uptake increased and thickened the film beneath the cantilever. This caused upward deflection of the cantilever, which lowered the electrical resistance in the circuit. As osmolality was stepped from 180- to 90 mOsm/Kg, and from 90- to 45 mOsm/Kg, the resistance decreased by 11 ohms and 7 ohms, respectively. This gave an average resistance change of 9 ohms for two-fold osmolality dilutions within this concentration range. Gravimetric swelling data (FIG. 1) show that the average stepwise change in swelling ratio corresponding to two-fold dilutions was 0.11 units. The reciprocal of this average is ~9 units, which correlates well with the resistance data.

Example 10

A hydrogel is prepared by polymerizing 10 grams of n-isopropyl acrylamide and 0.1 g acrylic acid in 50 ml of degassed water dimethyl formamide solution (1:1) at 70° C. using potassium persulfate as initiator. The resulting polymer is precipitated into 80° C. water, and dried to yield 9 grams of cold water soluble polymer. One gram of polymer is dissolved in 10 ml tetrahydrofuran and 0.001 g of Xama 2 is added to make a casting solution. The solution is used to prepare an imbedded microcantilever sensor as in example above and hydrated.

The sensor is placed in a solution of 0 mOsmol/kg solution and the resistance monitored as a function of temperature over the range 5° C. to 60° C. A transition is seen having a peak at approximately 37° C. The sensor is then placed in a water solution containing 500 ppm of carbon tetrachloride and the response over the same temperature range is measured. This time the peak in the transition will occur at a lower temperature. Using this method a calibration curve of carbon tetrachloride concentration versus transition temperature could be constructed.

A similar test is conducted using varying solution osmolality instead to develop a calibration curve of osmolality versus transition temperature.

An integrated MEMS sensor is readily constructed as an integrated device consisting of a piezoresistive microcantilever sensing element A, a sensing polymer B, a thermister C and a heating element D. All of these can be readily produced on a single silicon chip using known processing steps.

Example 11

A piezoresistive microcantilever sensor with integrated heating and temperature measurement capability is constructed by photo polymerizing approximately 100 µl of a solution of n-octaadecyl acryate, tripropylene glycol diacrylate (TPGDA, Sartomer) and Irgacure 184 (Ciba) (ratio 98.5: 1.0:0.5). The sensor is rinsed in 30° C. ethanol for 12 hours to remove residual monomers. The sensor will show a peak transition at 45° C. The solution is then placed in an 50° C. aqueous solution containing 500 ppm of toluene held for 30 minutes. The sensor is then retested and found to have a peak transition at 41° C.

The sensor can be exposed to the test solution above the peak temperature if desired to equilibrate more quickly, then quickly transferred to a temperature below the peak and measured as in this example or may be maintained below We its normal melting point while exposed to the analyte.

Example 12

Determining Effect of Osmolality on LCST of Osmotically Responsive Hydrogel

Preparation and Methods

An osmotically responsive polymer was prepared by casting a film from a solution containing hydroxypropyl acrylate prepolymer and diphenylmethane diisocyanate (1% weight per weight polymer solids). After curing, small pieces of the film were placed separately into each of four different osmolality test solutions. Hydrogels were allowed to swell to equilibrium (~48 hours) at room temperature. Immediately before scanning in the DSC, a hermetic pan was used to encapsulate ~10 mg of swollen hydrogel sample. The DSC (TA Instruments Model 2910) was programmed to scan between 5 and 80° C. at a rate of 5° C./min.

Results and Discussion

FIG. 17 shows the overlay plot of the DSC thermograms obtained for each of the samples. Table 3 below lists the thermal analysis data for each of the HPA samples. FIG. 18 contains graphs of the peak maximum and LCST data plotted according to the least-squares line fitting method.

The LCST at each osmolality was defined as the onset temperature of the endothermic peak in the corresponding DSC thermogram. Its value was calculated at the intersection point of two lines: one line drawn tangent to the original baseline and the other line drawn tangent to the curve's initial downward slope.

The hydrogel osmolality series (as shown in FIGS. 17 and 18, and Table 3) demonstrated the following trends in phase transition behavior:

The LCST and peak maximum temperatures occurred at lower temperatures for the higher osmolality gel solutions. The overall trend was that transition temperatures sequentially decreased as osmolality increased (with the exception of the 80 mOsm and 160 mOsm series, which exhibited identical LCST of 28° C.).

The transition enthalpy (delta H) decreased as osmolality increased.

Regression analysis showed that the peak maximum temperature and LCST correlated with osmolality with r=0.916 and r=0.883, respectively.

These results suggested that gels equilibrated at higher osmolality were less "extended" (swollen) than those equilibrated in lower osmolality solutions. Consequently, "shrinkage" or collapse of gel chains occurred at lower temperatures and required less heat energy.

TABLE 3

DSC Thermal Analysis Data for Crosslinked Hydroxypropyl Acrylate Hydrogels.

| Graph Symbol | Solution Osmolality (mOsm/Kg) | LCST (onset temperature, ° C.) | Peak Maximum (temperature, ° C.) | Delta H (J/g) (transition enthalpy) |
|---|---|---|---|---|
| ♦ | 320 | 16 | 30 | −132 |
| + | 160 | 28 | 43 | −158 |
| • | 80 | 28 | 48 | −555 |
| − | 45 | 37 | 57 | −593 |

Example 13

Resonator Based Phase Change Sensor

A piezoelectric microcantilever having a resonant frequency is dip coated with the polymer of example 7 containing 0.05% PFAZ and allowed to dry. The dried microcantilever is heated at 70° C. for 30 minutes to complete reaction and remove residual solvent. The coated piezoelectric cantilever is placed in a precision water temperature bath and the resonate frequency is measured as a function of temperature over the range of 20° C. to 60° C. The resonate frequency changes gradually up to about 45 degrees and after going through a step change at 48° C. then changes gradually again up to 60° C. The process is repeated in an aqueous solution containing 50, 100 and 400 ppm toluene giving progressively lower phase change temperatures.

Example 14

Phase Change Molecularly Imprinted Hydrogel Sensing Device

A commercially available tuning fork made from single crystal quartz and having tines 2 mm long, 200 microns wide, and 100 microns thick exhibited a quality factor of 3,000 in air. The resonant frequency of the resonators is ~32 kHz. A hydrogel precursor was prepared by polymerizing hydroxy propyl acrylate (8 g) 4-vinyl pyridine (1.5 g) and n-metholyl acrylamide (0.5 g) using persulfate initiator. The hydrogel precursor was taken up into a glass pipette and a small fiber of polymer solution was bridged across the two tines, allowed to dry for 5 minutes at 50% humidity. The sensor was then placed in a 2% copper sulfate solution containing 0.1% sulfuric acid for 5 minutes, rinsed in water and dried at 80° C. for three hours to allow the metholyl groups to condense creating a copper ion templated polymer. Subsequently the sensor was in placed 5 ml of de-ionized water to extract residual copper ions. The resulting sensor had enhanced selectivity for copper over zinc and cobalt ions.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A sensor device, comprising:
   a sensing material which responds to a change in osmolality of a solution by a change in volume, said sensing material comprising more than about 50% by weight of a polymerized hydroxypropyl acrylate monomer;
   a deformable arm comprising a first end connected to a substrate and a second end positioned such that it is moved in response to the volumetric change of the sensing material; and
   a signaling component which creates a detectable signal in response to deformation of the arm caused by movement of the second end of the arm.

2. The sensor device of claim 1, wherein the volumetric change is an increase in volume.

3. The sensor device of claim 1, wherein the sensing material undergoes a volumetric change of 50% or more in response to a change in osmolality.

4. The sensor of claim 1, wherein the sensing material is a hydrogel.

5. The sensor of claim 1, wherein the sensing material undergoes a phase transition in response to a change in osmolality.

6. The sensor device of claim 1, wherein the volumetric change is a decrease in volume.

7. The sensor device of claim 1, wherein the signaling component is chosen from a piezoresistor, a piezoelectric component, and a capacitor.

8. The sensor device of claim 7, further comprising:
   a source of voltage connected to the arm and applying an electrical potential difference between two points on the arm.

9. The sensor device of claim 8, further comprising:
   a meter connected to the arm capable of measuring a change in resistance of the piezoresistor.

10. The sensor device of claim 1, wherein the second end of the arm is positioned with a space between the second end and a surface of the sensing material.

11. The sensor device of claim 10, wherein the space is 1 millimeter or less.

12. The sensor device of claim 1, wherein the second end of the arm is connected to the sensing material.

13. The sensor device of claim 1, wherein the second end of the arm is positioned inside the sensing material.

14. The device of claim 1, wherein the sensing material comprises a receptor that selectively binds a target molecule, the receptor comprising a chemical moiety bound to the polymer sensing material.

15. The device of claim 14, wherein the chemical moiety is a hydroxyl chemical moiety on the polymer sensing material.

16. The device of claim 15, wherein the chemical moiety is a hydroxyl chemical moiety on a hydroxypropyl acrylate unit of the polymer sensing material.

* * * * *